US011806196B2

(12) United States Patent
Schuele et al.

(10) Patent No.: US 11,806,196 B2
(45) Date of Patent: Nov. 7, 2023

(54) HEAD STABILIZATION DEVICE WITH INCORPORATED MARKERS

(71) Applicant: pro med instruments GmbH, Freiburg Im Breisgau (DE)

(72) Inventors: Matthias E. Schuele, Freiburg (DE); Sascha Kubis, Freiburg (DE); Roman Maier, Scheer (DE)

(73) Assignees: pro med instruments GmbH, Freiburg im Breisgau (DE); Brainlab AG, Munich (DE)

( * ) Notice: Subject to any disclaimer, the term of this patent is extended or adjusted under 35 U.S.C. 154(b) by 717 days.

(21) Appl. No.: 16/934,443

(22) Filed: Jul. 21, 2020

(65) Prior Publication Data

US 2021/0022825 A1 Jan. 28, 2021

Related U.S. Application Data

(60) Provisional application No. 62/876,932, filed on Jul. 22, 2019.

(51) Int. Cl.
*A61B 34/30* (2016.01)
*A61B 90/14* (2016.01)
(Continued)

(52) U.S. Cl.
CPC .............. *A61B 90/14* (2016.02); *A61B 34/20* (2016.02); *A61B 90/36* (2016.02); *A61B 90/39* (2016.02);
(Continued)

(58) Field of Classification Search
CPC . A61B 19/201; A61B 19/203; A61B 19/5244; A61B 34/30; A61B 34/20;
(Continued)

(56) References Cited

U.S. PATENT DOCUMENTS 5,971,997 A 10/1999 Guthrie et al.
9,918,797 B2 3/2018 Birkenbach et al.
(Continued)

FOREIGN PATENT DOCUMENTS

EP 1 599 148 4/2011
WO WO 2004/075768 A2 10/2004

OTHER PUBLICATIONS

Screenshots from www.brainlab.com/surgery-products/overiew-neurosurgery-products, printed Apr. 26, 2021.
(Continued)

*Primary Examiner* — Vi X Nguyen
(74) *Attorney, Agent, or Firm* — Frost Brown Todd LLP

(57) ABSTRACT

A head stabilization device or HFD includes a plurality of integrated markers. The HFD may be in the form of a skull clamp, vacuum bag, combinations thereof, or other supporting structure. The integrated markers include MRI markers detectable by an MRI scanner and fiducial markers detectable by a registration tool of a navigation system. The markers provide a reference point relative to an operation site in a patient for use in a navigation guided procedure and aid in registering or calibrating the location of the patient with captured images used in the navigation guided procedure.

6 Claims, 17 Drawing Sheets

(51) Int. Cl.
    *A61B 34/20*     (2016.01)
    *A61B 90/00*     (2016.01)
    *A61B 90/50*     (2016.01)

(52) U.S. Cl.
    CPC ...... *A61B 90/50* (2016.02); *A61B 2034/2065* (2016.02); *A61B 2034/2068* (2016.02); *A61B 2090/363* (2016.02); *A61B 2090/3954* (2016.02); *A61B 2090/502* (2016.02)

(58) Field of Classification Search
    CPC ......... A61B 90/00; A61B 90/50; A61B 90/14; A61B 90/39; A61B 90/36
    See application file for complete search history.

(56) References Cited

U.S. PATENT DOCUMENTS

| | | |
|---|---|---|
| 10,908,238 B2 | 2/2021 | Gross et al. |
| 2011/0098553 A1* | 4/2011 | Robbins ................. A61B 5/055 |
| | | 600/410 |
| 2012/0060847 A1 | 3/2012 | Stratton et al. |
| 2012/0201421 A1* | 8/2012 | Hartmann ............ A61B 6/5235 |
| | | 382/103 |
| 2014/0275973 A1 | 9/2014 | Schuele |
| 2016/0106508 A1 | 4/2016 | Lathrop et al. |
| 2016/0259019 A1 | 9/2016 | Gross et al. |
| 2017/0319143 A1* | 11/2017 | Yu ......................... A61B 5/682 |

OTHER PUBLICATIONS

Screenshots from www.brainlab.com/surgery-products/overiew-platform-products/kick-Navigation, printed Apr. 26, 2021.

International Search Report and Written Opinion dated Feb. 24, 2021 for International Application No. PCT/IB2020/000605, 20 pages.

U.S. Appl. No. 17/959,710, filed Oct. 4, 2022.

European Search Report for EP 22207689.5 dated Feb. 27, 2023, 12 pages.

* cited by examiner

HEAD STABILIZATION DEVICE WITH INCORPORATED MARKERS

PRIORITY

This application claims priority to U.S. Provisional Patent App. No. 62/876,932, entitled "Head Stabilization Device with Incorporated Markers," filed Jul. 22, 2019, the disclosure of which is incorporated by reference herein.

BACKGROUND

The devices and methods disclosed pertain to patient stabilization, and in particular head and neck stabilization using stabilization devices known as head stabilization devices which are also referred to as head fixation devices (hereinafter referred to as "HFDs" or "HFD" in singular). HFDs are sometimes used during a variety of surgical and other medical procedures, for example during head or neck surgery or testing where it would be desirable to securely hold a patient's head in a certain position. HFDs are further sometimes used in conjunction with various imaging modalities, that may include imaging pre-procedure, during the procedure, and/or post-procedure. While a variety of stabilization devices have been made and used, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements.

Figure 1:
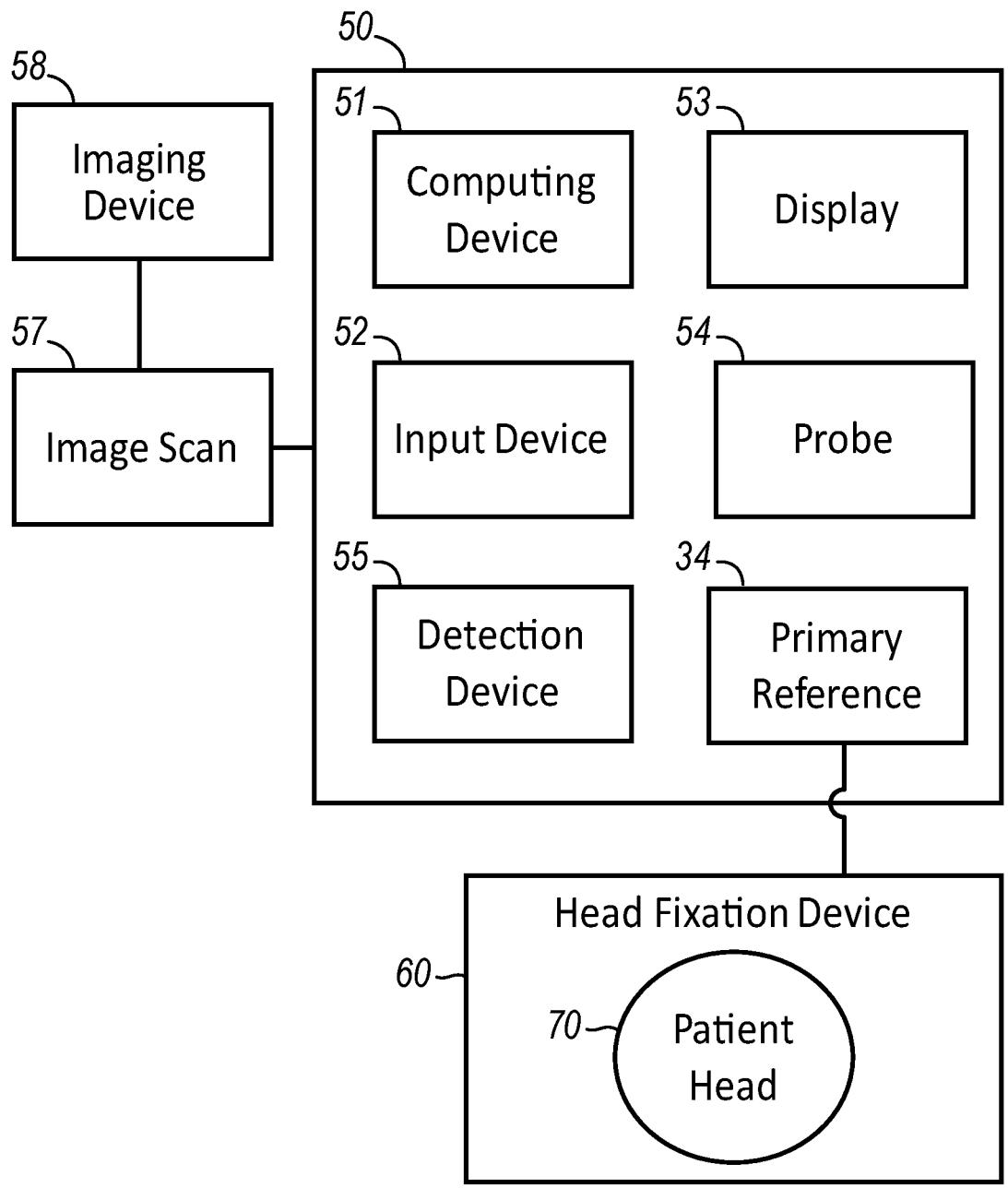
FIG. 1 depicts a schematic view of an exemplary surgical navigation system usable with the HFDs described herein.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Navigation Overview

In some versions, HFDs may be used in navigation guided procedures (i.e., for brain tumor removal or biopsy). In navigation procedures, navigation equipment and software systems are used in conjunction with imaging to provide accuracy in detecting and operating on a desired site within a head of a patient. With navigation procedures, various suitable types of imagining modalities can be used pre-operatively as well as intra-operatively and post-operatively. Such imaging modalities include but are not limited to magnetic resonance imaging (MRI), computed tomography (CT), x-ray, ultrasound, among others and combinations thereof.

One aspect of navigation guided procedures is a registration step or process to associate the pre-operative image used for procedure planning with the physical or spatial location of the patient's head during the procedure. By making this association or registration, the navigation software can match the real time location of the patient's head during the procedure with the pre-operative image to display a spatial map of the surgical site to the surgeon during the procedure. Because the images used for planning are captured earlier than the procedure, to register the patient with the earlier images, a common set of data points is needed between the patient's spatial location and the image of the patient in the pre-operative image. With identified common data points in both the pre-operative image and the patient's spatial location during the procedure, the navigation system's software registers the patient with the image and creates the spatial map. Thereafter, live movement of the instruments and/or probes used during the procedure may be shown relative to the pre-operative images on the display to provide accurate navigation relative to the desired operation site within the head of the patient.

In some navigation guided procedures, fiducial markers are applied or adhered to a patient's head area for the purpose of registration. These markers may be detectable by the navigation system and then combined with pre-operative images of the patient's head to create a spatial map of the patient's head, including the desired operation site. For example, the navigation system may include a probe, the location of which is detectable by or otherwise in communication with the navigation system such that the tip of the probe's location is determinable by the navigation system software. The probe is useable to locate the applied markers by the operator using the probe to touch each marker and thereby communicating the location of each applied marker to the navigation system's software. Furthermore, these fiducial markers may be applied to the patient at locations that correlate with features appearing in the pre-operative image such that the common data set mentioned above for registration is realized. Although not required, in some instances these fiducial markers are applied prior to acquiring the pre-operative image such that the fiducial markers appear in the pre-operative image. In some other versions, these fiducial markers can be omitted and instead registration can use anatomical features of the patient that appear in the pre-operative image. For instance, the probe may be configured to locate the tip of the patient's nose, ear openings, certain bone structure, and other features that can then be matched with the pre-operative image to create the spatial map. In these instances, the probe may be configured as an optical scanning device.

In some versions, navigation system software uses an optical camera system to locate and identify a primary active or passive reference or marker that provides a reference for the navigation system. In some instances, the primary reference may be referred to as a "star reference," or other name to distinguish it from other markers. An active primary reference may emit a detectable feature, such as light, etc. that the optical camera system can detect. A passive primary reference is detectable without emitting anything or being powered in some manner. For instance, a passive primary reference can be detectable based on its light reflective properties, shape or configuration. By way of example only, in a navigation system, an optical camera system may be programmed to recognize the primary reference after the patient has been secured with the HFD to define a reference for the navigation system. Thereafter, with multiple fiducial markers in place on the patient, a registration tool of the system, i.e., a probe, can be used to provide the navigation software with the location of these fiducial markers—or anatomical features where those are used instead of fiducial markers applied to the patient. Once located, the navigation system's software can record the relative location of the fiducial markers to the primary or star reference. As will be appreciated by those of ordinary skill in the art, the above example of a navigation software system is merely one example.

By way of example only, and not limitation, FIG. 1 depicts an exemplary schematic view of a navigation system (50) usable with an HFD (60) securing a patient's head (70) for navigation guided surgical procedures. Navigation system (50) is exemplary only and other navigation systems usable with the HFDs described herein may include different or additional features as will be appreciated by those of ordinary skill in the art in view of the teachings herein. In the present example, navigation system (50) includes a computing device (51) with an input device (52) such as a keyboard, pointer device, touchscreen, etc., and a display (53) such as a monitor, projector, etc. In some instances, input device (52) is a touchscreen interface that is part of display (53). Computing device (51) is equipped with navigation software which may be locally saved on computing device (51) or accessible from a remote networked location. Computing device (51) further includes a processor, a memory, a storage volume, a power source, etc. such that computing device (51) is operable to execute the programs associated with the navigation software.

Navigation system (50) further includes a primary reference (34), a probe (54) and a detection device (55), which may be an optical camera system as described above. Probe (54) is detectable by or in communication with navigation system (50), and in one example this detection by navigation system (50) occurs via detection device (55) detecting probe (54) and detection device (55) communicating location data to computing device (51). More specifically the precise location of a tip of probe (54) is identified and trackable by navigation system (50). Probe (54) can be touched to the patient's head or face to acquire data points of the patient's anatomy that may also appear in an image scan (57) that was previously acquired by an imagine device (58) and uploaded to navigation system (50). Imaging device (58) may be an MRI device, CT scanner, X-ray machine, or other imaging modality as will be apparent to those of ordinary skill in the art in view of the teachings herein. As mentioned above, in some examples fiducial markers may be applied to the patient and used as reference points instead of or in addition to the patient's anatomical features providing such points of reference. In this manner, the patient's spatial location or position can be registered to image scan (57), which may be the pre-operative planning image as described above. The navigation software is operable to manipulate and show image scan (57) on display (53) for viewing.

With the initial patient registration completed, sterile drapes are used during the procedure to minimize infection risk. These drapes conceal any applied fiducial markers and those anatomical features of the patient that were used during the initial registration process. Moreover, during procedures it may be necessary to re-register the patient with the navigation system. For instance, if there is a loss of power, or movement of the equipment or patient, re-registration would be needed. In some instances, after opening the skull, an updated image is obtained to check for or confirm there was no brain shift phenomenon that occurred when opening the skull. In these instances, re-registration would be needed after taking the updated image. Re-registration would also be needed if the patient were moved to obtain updated images to check procedure progress against the pre-operative images. For instance, for tumor resection an intra-operative scan may be taken to confirm tumor location and/or complete tumor resection. In any case however, the sterile draping can limit the ability to effectively use probe (54) to acquire patient anatomical data points (or access to fiducial markers adhered to the patient if those are used) to complete the registration as was done previously prior to draping and beginning the surgical procedure. The devices and methods described below provide ways to accomplish re-registration of the patient manually or automatically when re-registration is needed, without compromising the sterile environment and draping that may be in place.

II. Exemplary Skull Clamp HFDs with Integrated Markers

Figure 2:
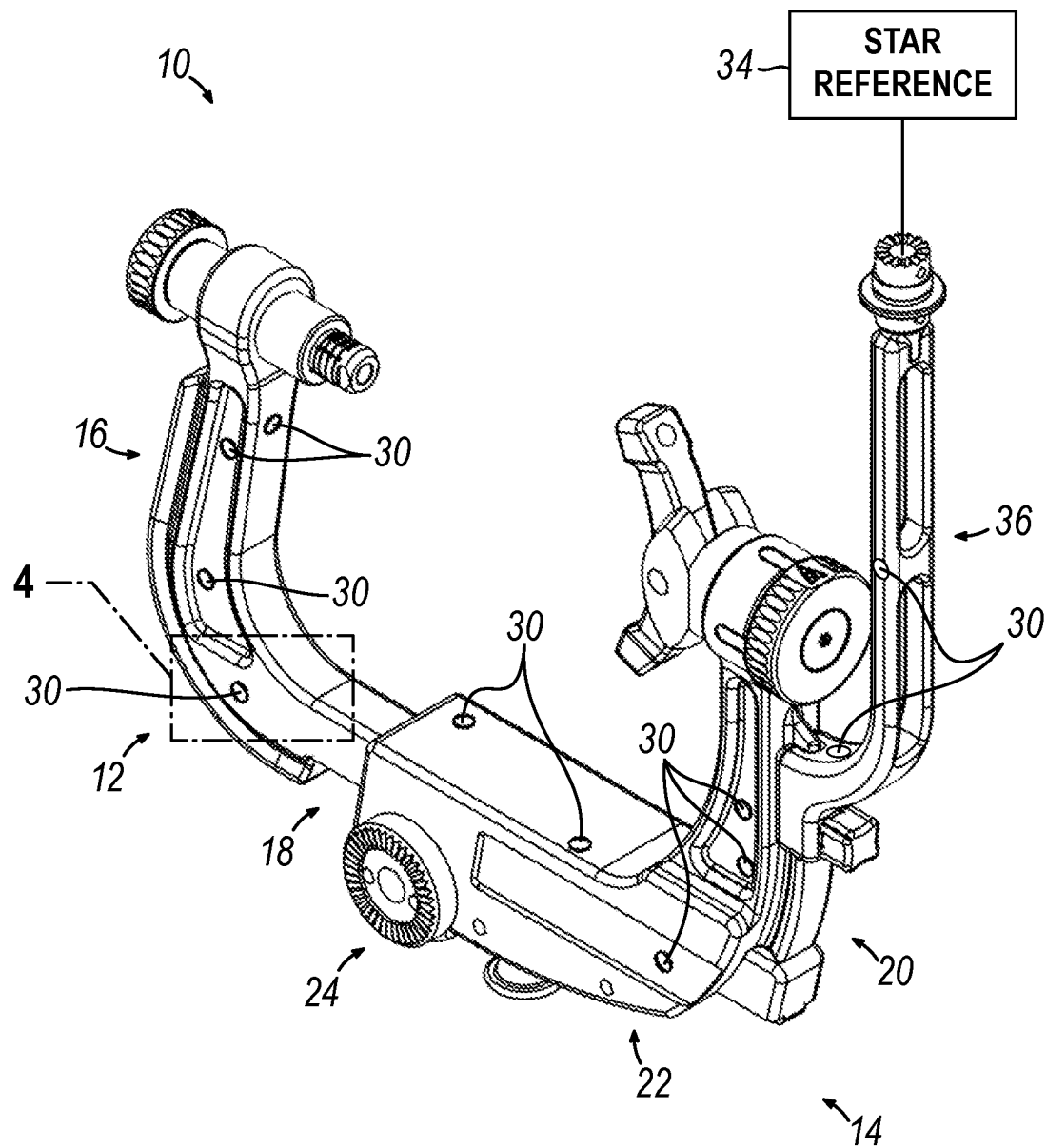
FIG. 2 depicts a front perspective view of a first exemplary HFD in the form of a skull clamp comprising integrated MRI markers.
Figure 3:
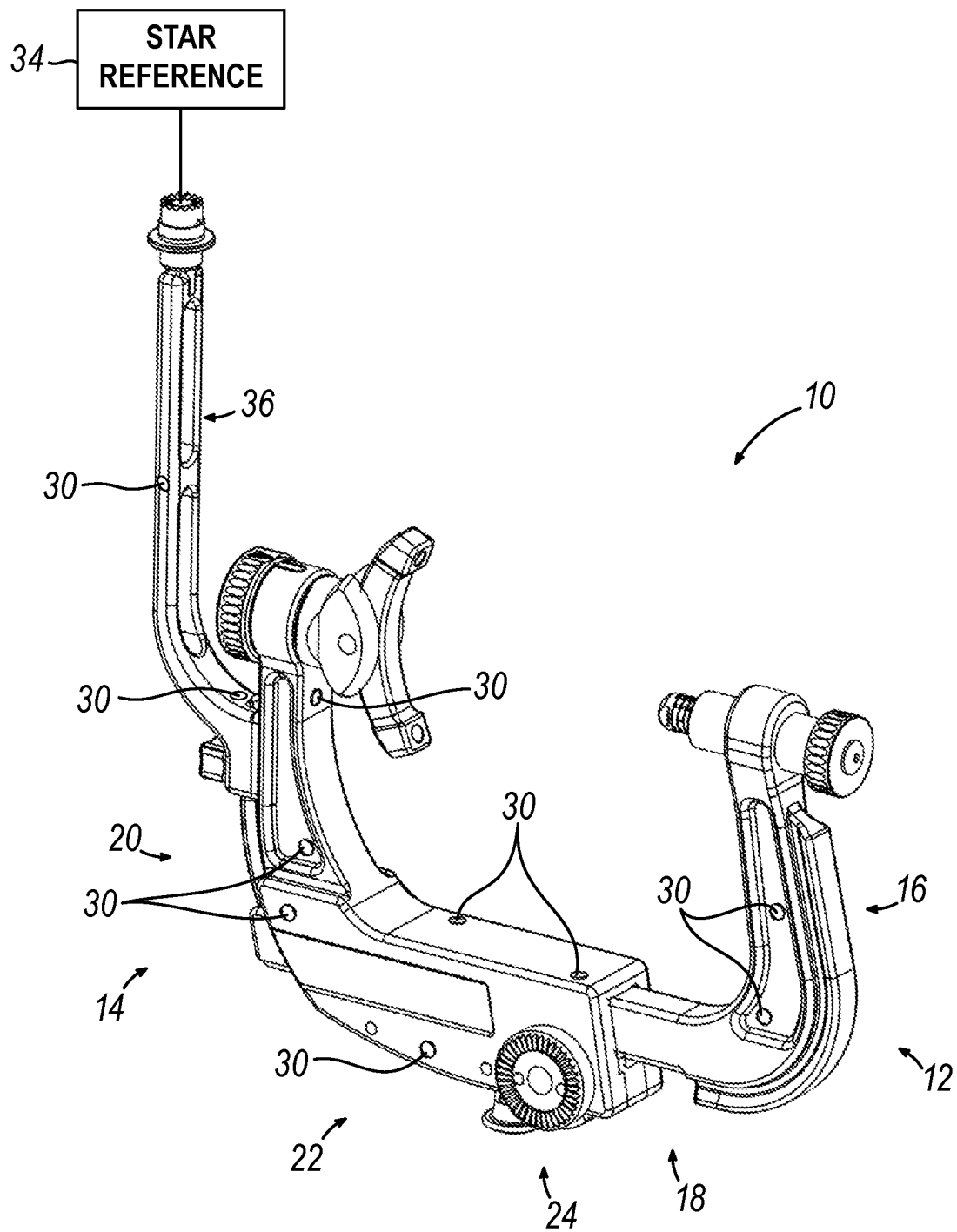
FIG. 3 depicts a rear perspective view of the HFD of FIG. 2.
Figure 4:
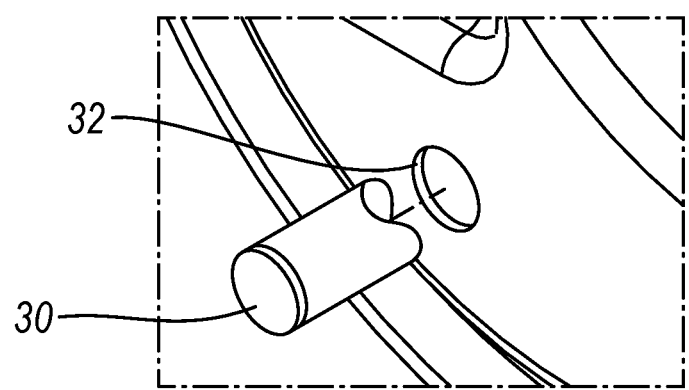
FIG. 4 depicts an enlarged view of the HFD of FIG. 2, taken within area 4 in FIG. 2, showing a marker disassembled from a corresponding recess of the HFD.

FIGS. 2-4 illustrate a first exemplary HFD in the form of a skull clamp (10). While the present example illustrates the HFD as a U-shaped skull clamp, the teachings herein may be applied to other forms of HFDs as will be understood by those of ordinary skill in the art in view of the teachings herein. Skull clamp (10) comprises a first arm (12) and a second arm (14). First arm (12) is connectable with second arm (14) to form skull clamp (10) having a U-shape. First arm (12) comprises an upright portion (16) and a lateral portion (18). Similarly, second arm (14) comprises an upright portion (20) and a lateral portion (22). Skull clamp (10) is adjustable to accommodate a variety of head sizes by translating first arm (12) relative to second arm (14) or vice versa. Skull clamp (10) is further connectable to other structures, such as a positioning adapter or a base unit that is further connectable with an operating table, etc., by way of an attachment interface (24).

In the present example, skull clamp (10) is constructed of radiolucent material such that skull clamp (10) is compatible with various imaging modalities. Skull clamp (10) comprises a plurality of integrated markers (30). Markers (30) are positioned about first and second arms (12, 14) of skull clamp (10). As best seen in FIG. 4, skull clamp (10) comprises a recess (32) extending within skull clamp (10) for receiving a marker (30). Marker (30) may thereby be flush with an exterior surface of skull clamp (10) when marker (30) is inserted within a recess (32). While markers (30) are shown as being cylindrical, any other suitable shape may be used. Markers (30) are thereby positioned about a head while the head is positioned in skull clamp (10). Markers (30) are compatible with MRI such that they are detectable in a manner with little artifacts or distortion when seen in the MM output. For example, markers (30) may be constructed of any suitable material that interferes with a magnetic field of an MRI scanner. In this regard, markers (30) are considered MRI markers or sometimes referred to as MR markers. In some versions, markers (30) are also detectable in other imaging modalities, such as computed tomography (CT), x-ray, ultrasound, and combinations thereof. Accordingly, in the present example, intra-operative scans can be taken by an Mill scanner such that images of a brain can be obtained while the head is positioned within skull clamp (10), and markers (30) will be apparent in the imaging output.

As shown schematically in FIGS. 2-3, a primary active or passive reference or a star reference (34) detectable by an optical camera system of the navigation system or other detection device may also be used with skull clamp (10) to provide a reference point of each marker (30) relative to primary or star reference (34). For instance, star reference (34) may be selectively connected to an interface at a top portion of a support arm (36) extending outwardly from skull clamp (10). Support arm (36) is selectively attached or connected with skull clamp (10) in the present example; however, in other versions support arm (36) is permanently connected with skull clamp (10) or is formed as part of skull clamp (10). Accordingly, primary reference (34) itself, or along with support arm (36), may be removed during an intra-operative image procedure, and then reattached after for continued navigation guidance. Furthermore, this re-attachment is configured such that primary reference (34) attaches in the same location each time relative to HFD (10) and the patient. Accordingly, once the camera system or other detection device detects primary reference marker (34) after attachment with skull clamp (10), the location of markers (30) are known by the navigation system. This is so because the navigation system software is programmed prior to the procedure to know the configuration of skull clamp (10), including the location or coordinates of markers (30) relative to the primary reference (34). The navigation system may also include relative location data among various markers (30) themselves based on programmed information about skull clamp (10) being input into the navigation system's software.

In an exemplary use, a patient has a pre-operative image obtained prior to the procedure and without the use of skull clamp (10). With the pre-operative image input provided to the navigation system, and with the patient secured with head clamp (10), the initial registration steps can be completed as described above such that the spatial location or position of the patient is correlated or matched to the pre-operative image input to the navigation system. For instance, the anatomical features of the patient can be scanned or touched-off and correlated with those features in common with the pre-operative image to achieve initial patient registration as described above.

After draping the patient and procedure environment, the procedure can begin with the skull being opened to access the surgical site. At some point, another image may be desired for one or more of the reasons mentioned above. With the patient draped and secured within skull clamp (10), the patient can be moved to the imaging device and the image can be captured, e.g., via MRI. Before resuming the surgical procedure, the patient is returned to the operating location and re-registered with the navigation system.

In instances where the patient is re-registered with the pre-operative image, detection of primary reference marker

(34) by the camera system or other detection device automatically re-registers the patient with the pre-operative image without the need to disturb the sterile drapes. As mentioned above, the location and orientation of the patient is known relative to primary reference (34) based on the initial registration steps. Accordingly, when the optical camera locates primary reference (34), the navigation system's software can re-register the patient with the pre-operative image.

In some instances, it may be desirable to register the patient with the updated intra-operative image acquired. For instance, this may be so when checking tumor resection and identifying further area for resection based on an intra-operative image scan. With the intra-operative image that includes skull clamp (10), markers (30) are detected in the imaging and appear in the image output that is provided to the navigation software. Because the location of markers (30) relative to primary reference marker (34) is known, the detection of primary reference marker (34) by the optical camera or other detection device of the navigation system allows the navigation software to associate the spatial location of markers (30) with the updated intra-operative image showing markers (30) in the image output. Accordingly, the navigation software obtains updated image data on the operation site within the patient's head and its spatial location relative to markers (30) and the patient's head because the patient's head is fixed relative to markers (30) with the patient is secured within skull clamp (10). With the re-registration processes described above using markers (30), there is no need to disturb the sterile draping to use a probe and locate either fiducial markers applied to the patient, or anatomical features of the patient's head when re-registering the patient with the navigation system.

Figure 5:
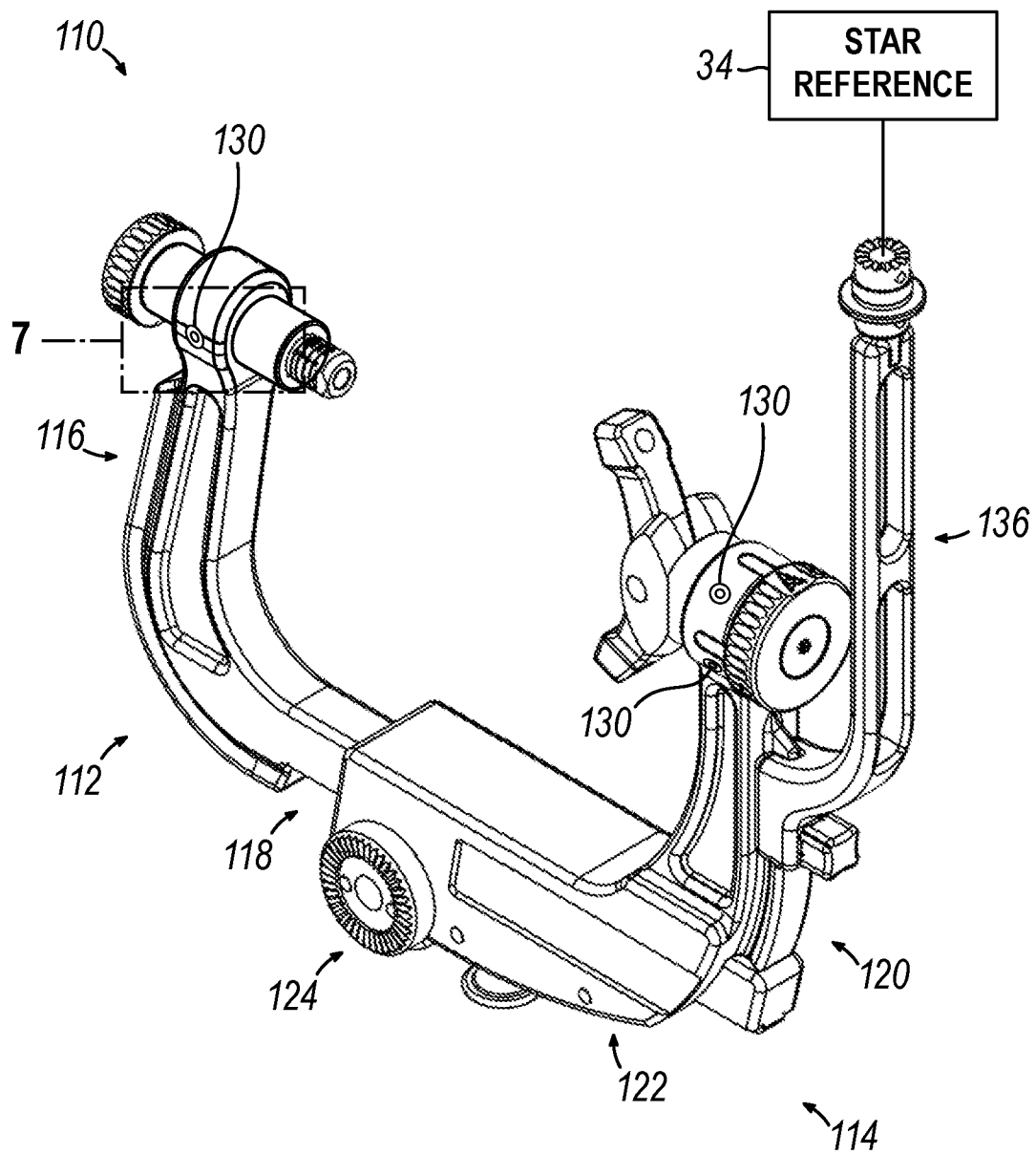
FIG. 5 depicts a front perspective view of a second exemplary HFD in the form of a skull clamp comprising integrated fiducial markers.
Figure 6:
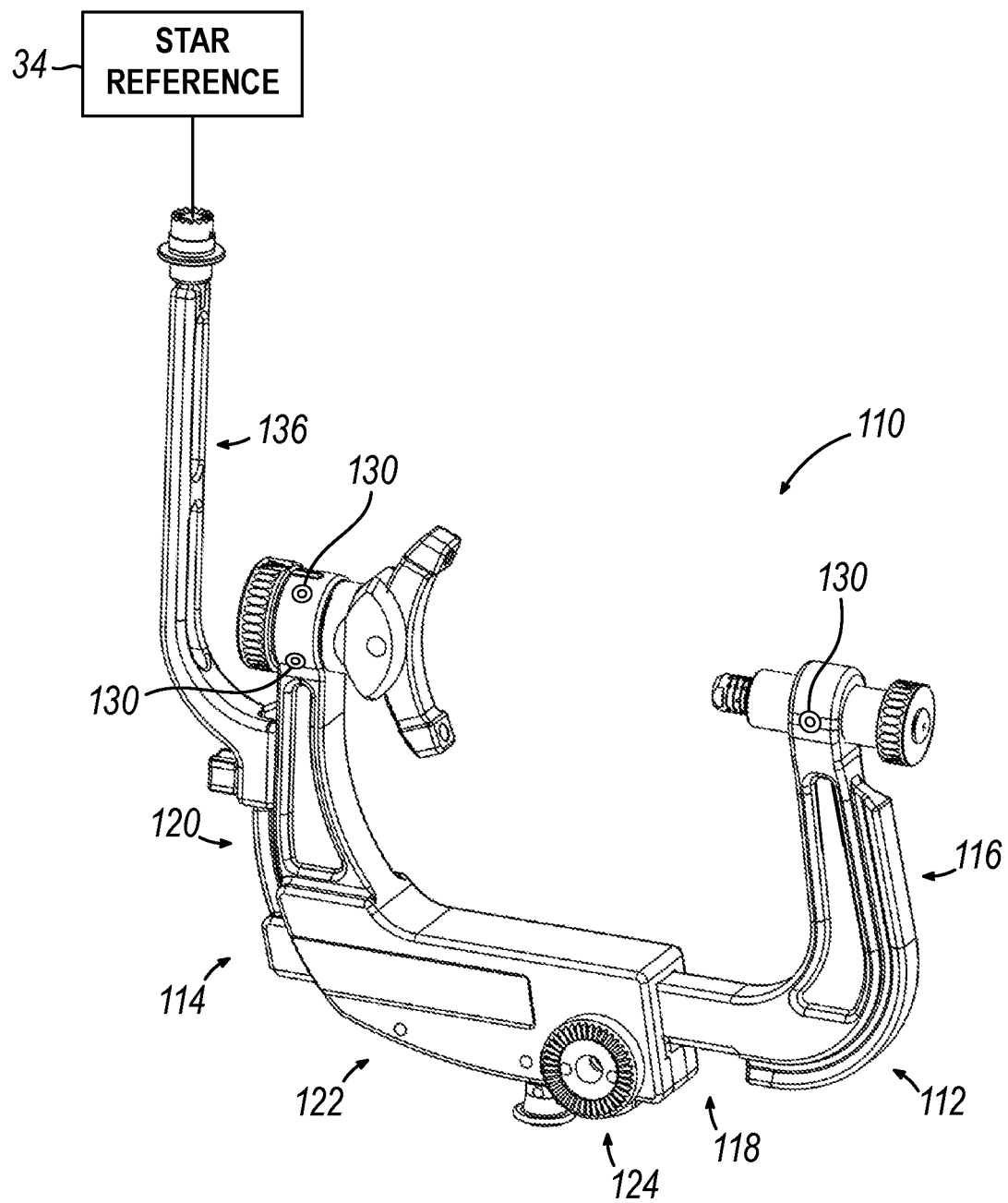
FIG. 6 depicts a rear perspective view of the HFD of FIG. 5.
Figure 7:
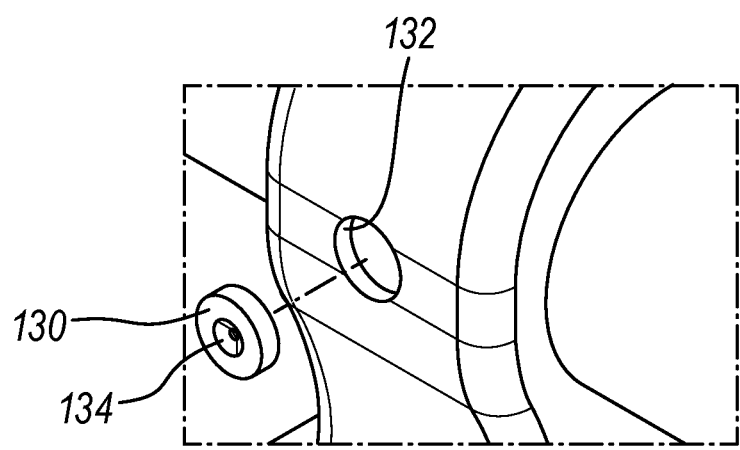
FIG. 7 depicts an enlarged view of the HFD of FIG. 5, taken within area 9 in FIG. 5, showing a marker disassembled from a corresponding recess of the HFD.

Referring to FIGS. 5-7, a second exemplary HFD in the form of a skull clamp (110) is shown. While the present example illustrates the HFD as a U-shaped skull clamp, the teachings herein may be applied to other forms of HFDs as will be understood by those of ordinary skill in the art in view of the teachings herein. Skull clamp (110) comprises a first arm (112) and a second arm (114). First arm (112) is connectable with second arm (114) to form skull clamp (110) having a U-shape. First arm (112) comprises an upright portion (116) and a lateral portion (118). Similarly, second arm (114) comprises an upright portion (120) and a lateral portion (122). Skull clamp (110) is adjustable to accommodate a variety of head sizes by translating first arm (112) relative to second arm (114) or vice versa. Skull clamp (110) is further connectable to other structures, such as a positioning adapter or a base unit that is further connectable with an operating table, etc., by way of an attachment interface (124).

In some versions skull clamp (110) is constructed of radiolucent material such that skull clamp (110) is compatible with various imaging modalities. In other versions skull clamp (110) is non-radiolucent. Skull clamp (110) comprises integrated markers (130). Skull clamp (110) is similar to skull clamp (10), except that markers (130) of skull clamp (110) are fiducial markers that may be detectable by a registration tool of a navigation system. For example, markers (130) comprise haptic landmarks which may be tapped by the registration tool in a predetermined sequence to perform registration. In some versions, markers (130) are also detectable by scanning modalities, such as MRI, CT, x-ray, ultrasound, or combinations thereof, but this is not required in all cases. Markers (130) are positioned about first and second arms (112, 114) of skull clamp (110). In the illustrated version, on each side of skull clamp (110) a pair of markers (130) are located along a dual pin holder assembly. Furthermore, on each side of skull clamp (110) a marker (130) is located at an upper part of arm (112) aligned with a single pin holder assembly. In view of the teachings herein, other locations for markers (130) will be apparent to those of ordinary skill in the art.

As best seen in FIG. 7, skull clamp (110) comprises a recess (132) extending within skull clamp (110) for receiving a marker (130). Marker (130) may thereby be flush with an exterior surface of skull clamp (110) when marker (130) is inserted within a recess (132). Markers (130) are thereby positioned about a head while the head is clamped or pinned in skull clamp (110). Fiducial markers (130) may be used with a navigation software system to register the spatial location of the patient's head with pre-operative and intra-operative images of the patient's head. Markers (130) comprise a recess (134), which may be conical, such that a probe seats properly and precisely within marker (130) when setting up spatial recognition. While markers (130) are shown as being cylindrical, any other suitable shape may be used.

As shown schematically in FIGS. 5 and 6, a primary active or passive reference or a star reference (34) detectable by an optical camera system of the navigation system or other detection device may also be used with skull clamp (110) to provide a reference point of each marker (130) relative to primary or star reference (34). For instance, star reference (34) may be selectively connected to an interface at a top portion of a support arm (136) extending outwardly from skull clamp (110). Support arm (136) is selectively attached or connected with skull clamp (110) in the present example; however, in other versions support arm (136) is permanently connected with skull clamp (110) or is formed as part of skull clamp (110). Accordingly, primary reference (34) itself, or along with support arm (136), may be removed during an intra-operative image procedure, and then reattached after for continued navigation guidance. Furthermore, this re-attachment is configured such that primary reference marker (34) attaches in the same location each time relative to HFD (110) and the patient. Accordingly, once the camera system or other detection device detects primary reference marker (34) after attachment with skull clamp (110), the location of markers (130) are known by the navigation system. This is so because the navigation system software is programmed prior to the procedure to know the configuration of skull clamp (110), including the location or coordinates of markers (130) relative to the primary reference (34). The navigation system may also include relative location data among various markers (130) themselves based on programmed information about skull clamp (110) being input into the navigation system's software.

In an exemplary use, a patient has a pre-operative image obtained prior to the procedure and without the use of skull clamp (110). With the pre-operative image input provided to the navigation system, and with the patient secured with head clamp (110), the initial registration steps can be completed as described above such that the spatial location or position of the patient is correlated or matched to the pre-operative image input to the navigation system. As a part of the initial registration, the location of markers (130) of skull clamp (110) are provided to the navigation system's software, for example by using a probe or pointer device of the navigation system as described above. The navigation system may also include relative location data among markers (130) based on programmed information about skull clamp (110) being input into the navigation system's software. In this manner, while locating markers (130) with probe to identify their location to the navigation system, the relative position of markers (130) to one another can be checked or confirmed against the known information in the navigation system. By locating markers (130) in the initial registration of the patient, the location of markers (130) is known relative to the pre-operative image and the patient. Additionally, the location of markers (130) is known relative to primary reference (34). Accordingly, the pre-operative image of the patient is registered with the patient by way of the anatomical features, and markers (130) provide a secondary set of data for possible subsequent registration of the patient securely positioned within skull clamp (10) as discussed below.

After draping the patient and procedure environment, the procedure can begin with the skull being opened to access the surgical site. At some point, another image may be desired for one or more of the reasons mentioned above. With the patient draped and secured within skull clamp (110), the patient can be moved to the imaging device and the image can be captured, e.g., via MRI or CT. Before resuming the surgical procedure, the patient is returned to the operating location and re-registered with the navigation system.

In instances where the patient is re-registered with the pre-operative image, detection of primary reference marker (34) by the camera system or other detection device automatically re-registers the patient with the pre-operative image without the need to disturb the sterile drapes. Accordingly, when the optical camera locates primary reference (34), the navigation system's software can re-register the patient with the pre-operative image. As mentioned above, the location and orientation of the patient is known relative to primary reference marker (34) based on the initial registration steps. Accordingly, when the optical camera locates primary reference (34), the navigation system's software can re-register the patient with the pre-operative image.

In some instances, it may be desirable to register the patient with the updated intra-operative image acquired. For instance, this may be so when checking tumor resection and identifying further area for resection based on an intra-operative image scan. With the intra-operative image that includes skull clamp (110), markers (130) are not necessarily detected in the imaging and thus do not necessarily appear in the image output that is provided to the navigation software. However, because the location of markers (130) relative to primary reference marker (34) is known, the detection of primary reference marker (34) by the optical camera or other detection device of the navigation system allows the navigation software to associate the spatial location of markers (130) with the updated intra-operative image.

In another example of re-registration to an intraoperative image, based on the configuration of markers (130), re-registration can be performed in a similar manner to the initial registration in the non-sterile setup, but now in the sterile setup. For instance, the probe can be used to locate and touch-off on markers (130) even with the drapes in place so as to not compromise the sterile setup. The haptic landmarks of markers (130) aid in being able to use the probe with markers (130) despite markers (130) being covered by a drape.

In instances where markers (130) may be detectable by an imaging modality and appearing in the intra-operative image output, re-registration of the patient to the navigation system using the updated intra-operative image may be achieved in the same manner as described above with respect to skull clamp (10) with markers (30).

Figure 8:
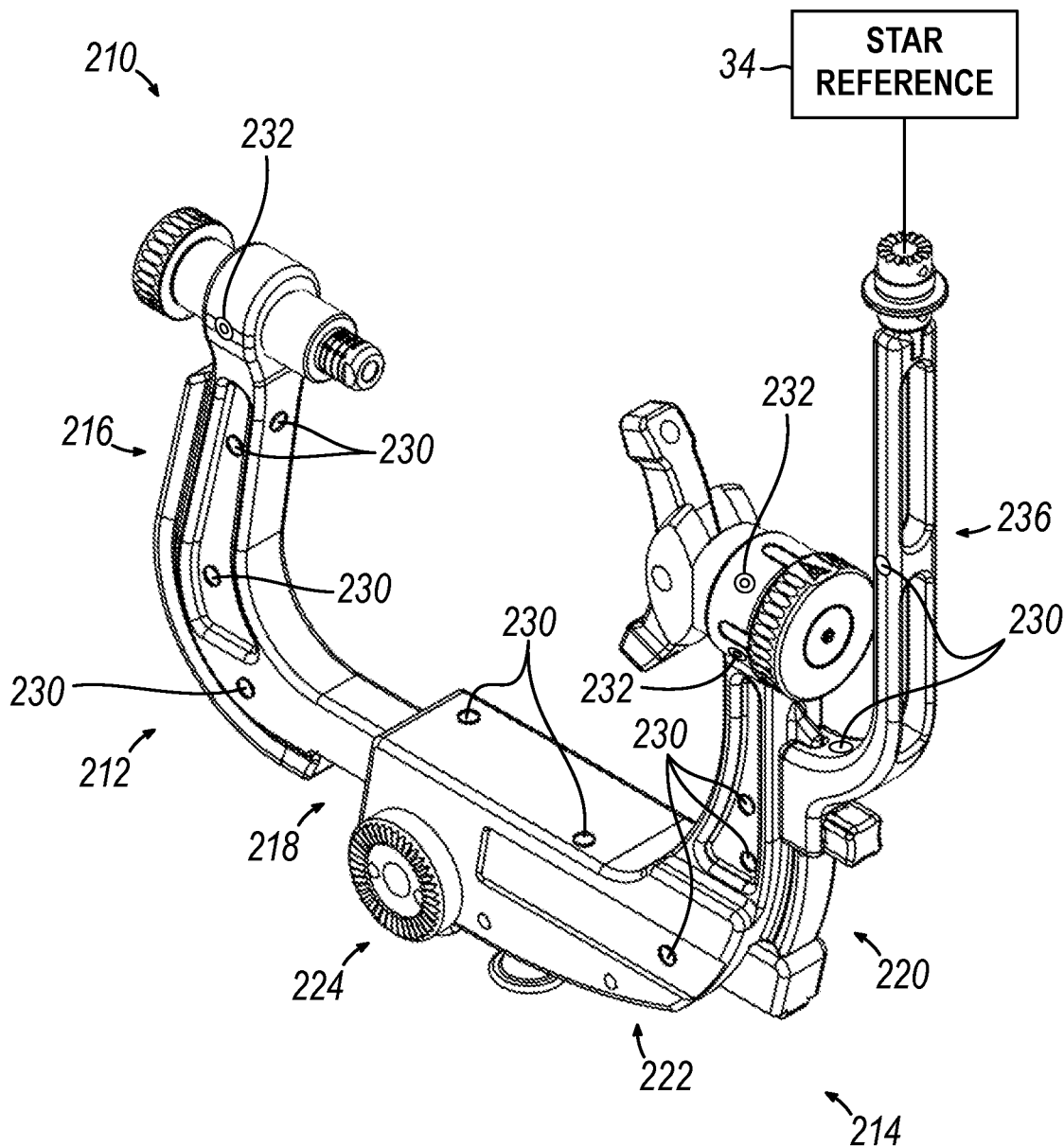
FIG. 8 depicts a front perspective view of a third exemplary HFD in the form of a skull clamp comprising integrated MRI markers and integrated fiducial markers.
Figure 9:
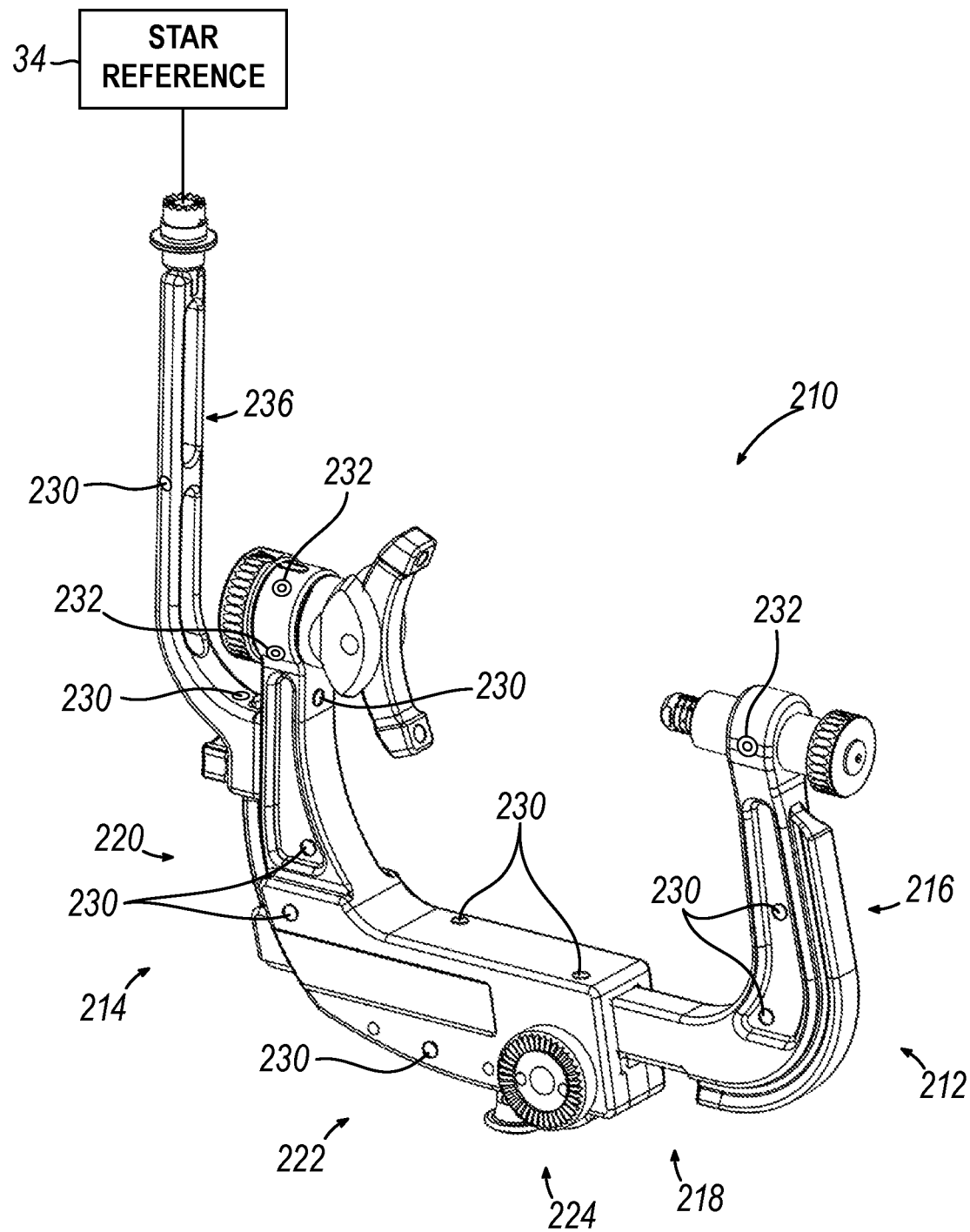
FIG. 9 depicts a rear perspective view of the HFD of FIG. 8.

FIGS. 8 and 9 show a third exemplary HFD in the form of a skull clamp (210). While the present example illustrates the HFD as a U-shaped skull clamp, the teachings herein may be applied to other forms of HFDs as will be understood by those of ordinary skill in the art in view of the teachings herein. Skull clamp (210) comprises a first arm (212) and a second arm (214). First arm (212) is connectable with second arm (214) to form skull clamp (210) having a U-shape. First arm (212) comprises an upright portion (216) and a lateral portion (218). Similarly, second arm (214) comprises an upright portion (220) and a lateral portion (222). Skull clamp (210) is adjustable to accommodate a variety of head sizes by translating first arm (212) relative to second arm (214) or vice versa. Skull clamp (210) is further connectable to other structures, such as a positioning adapter or a base unit that is further connectable with an operating table, etc., by way of an attachment interface (224).

Figure 12:
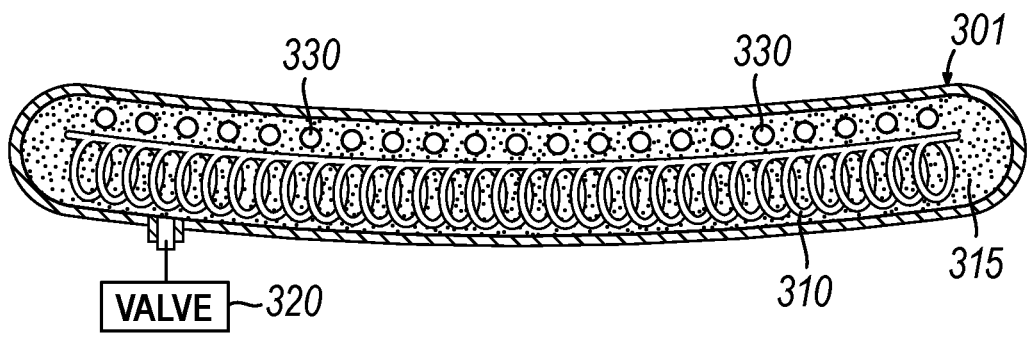
FIG. 12 depicts a cross-sectional view of another exemplary conforming bag for use with the skull clamp of FIG. 10, showing both an MRI coil and MRI markers disposed within the bag.
Figure 13:
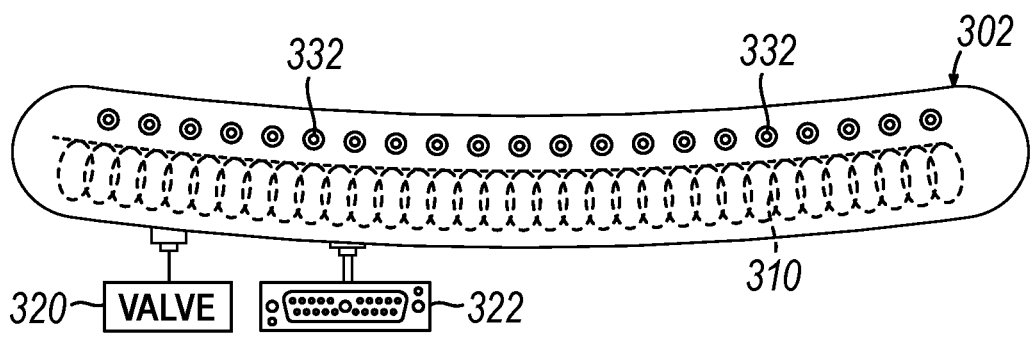
FIG. 13 depicts a side view of another exemplary conforming bag for use with the skull clamp of FIG. 10, showing both an MM coil disposed within the bag and fiducial markers located on the outside surface of the bag.
Figure 14:
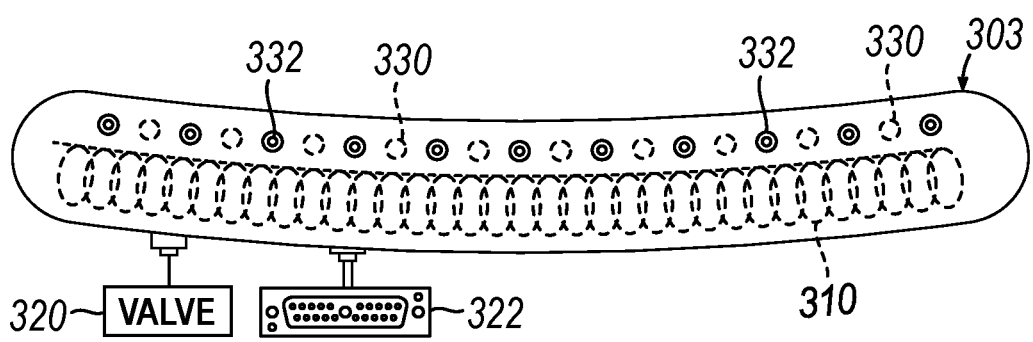
FIG. 14 depicts a side view of another exemplary conforming bag for use with the skull clamp of FIG. 10, showing both an MRI coil and Mill markers disposed within the bag and fiducial markers located on the outside surface of the bag.

In some versions, skull clamp (210) is constructed of radiolucent material such that skull clamp (210) is compatible with various imaging modalities. In other versions skull clamp (210) is non-radiolucent. Skull clamp (210) comprises a plurality of integrated markers (230, 232). Skull clamp (210) is similar to skull clamps (10, 110), except that skull clamp (210) comprises MRI markers (230) that are detectable by an MRI scanner and fiducial markers (232) that are detectable by a registration tool of a navigation system. Markers (230, 232) are positioned about first and second arms (212, 214) of skull clamp (210) as shown in FIGS. 12-14. Markers (230, 232) are thereby positioned about a head while the head is positioned in skull clamp (210). The combination of MRI markers (230) and fiducial markers (232) allow for registration and/or re-registration of a patient using either MRI markers (230) and/or fiducial markers (232). In this way, skull clamp (210) may be used in multi-modal imaging and provide the ability of re-registration as described above. For instance, where MRI markers (230) are used with MRI, automatic re-registration may be used as mentioned above. Where a CT scan is used instead of MRI, fiducial markers (232) are used for re-registration as mentioned above with respect to skull clamp (110). In some other versions, markers (232) are detectable by MRI in addition to serving as fiducial markers. In such versions with this feature for markers (232), markers (230) may be omitted, or may be included.

As shown schematically in FIGS. 8 and 9, a primary active or passive reference or a star reference (34) detectable by an optical camera system of the navigation system or other detection device may also be used with skull clamp (210) to provide a reference point of each marker (230, 232) relative to primary or star reference (34). For instance, star reference (34) may be selectively connected to an interface at a top portion of a support arm (236) extending outwardly from skull clamp (210). Support arm (236) is selectively attached or connected with skull clamp (210) in the present example; however, in other versions support arm (236) is permanently connected with skull clamp (210) or is formed as part of skull clamp (210). Accordingly, primary reference (34) itself, or along with support arm (236), may be removed during an intra-operative image procedure, and then reattached after for continued navigation guidance. Furthermore, this re-attachment is configured such that primary reference marker (34) attaches in the same location each time relative to HFD (210) and the patient. Accordingly, once the camera system or other detection device detects primary reference marker (34) after attachment with skull clamp (210), the location of markers (230, 232) are known by the navigation system. This is so because the navigation system software is programmed prior to the procedure to know the configuration of skull clamp (210), including the location or coordinates of markers (230, 232) relative to the primary reference (34). The navigation system may also include relative location data among various markers (230, 232) themselves based on programmed information about skull clamp (210) being input into the navigation system's software.

In an exemplary use, a patient has a pre-operative image obtained prior to the procedure and without the use of skull clamp (210). With the pre-operative image input provided to the navigation system, and with the patient secured with head clamp (210), the initial registration steps can be completed as described above such that the spatial location or position of the patient is correlated or matched to the pre-operative image input to the navigation system. Thereafter, skull clamp (210) with both types of markers—MR markers and fiducial markers—can be used for subsequent re-registration of the patient to pre-operative or intra-operative images in the same ways described above with respect to skull clamp (10) with MR markers (30), and/or skull clamp (110) with fiducial markers (130).

III. Exemplary Conforming Bags Usable with Skull Clamp HFDs

Figure 10:
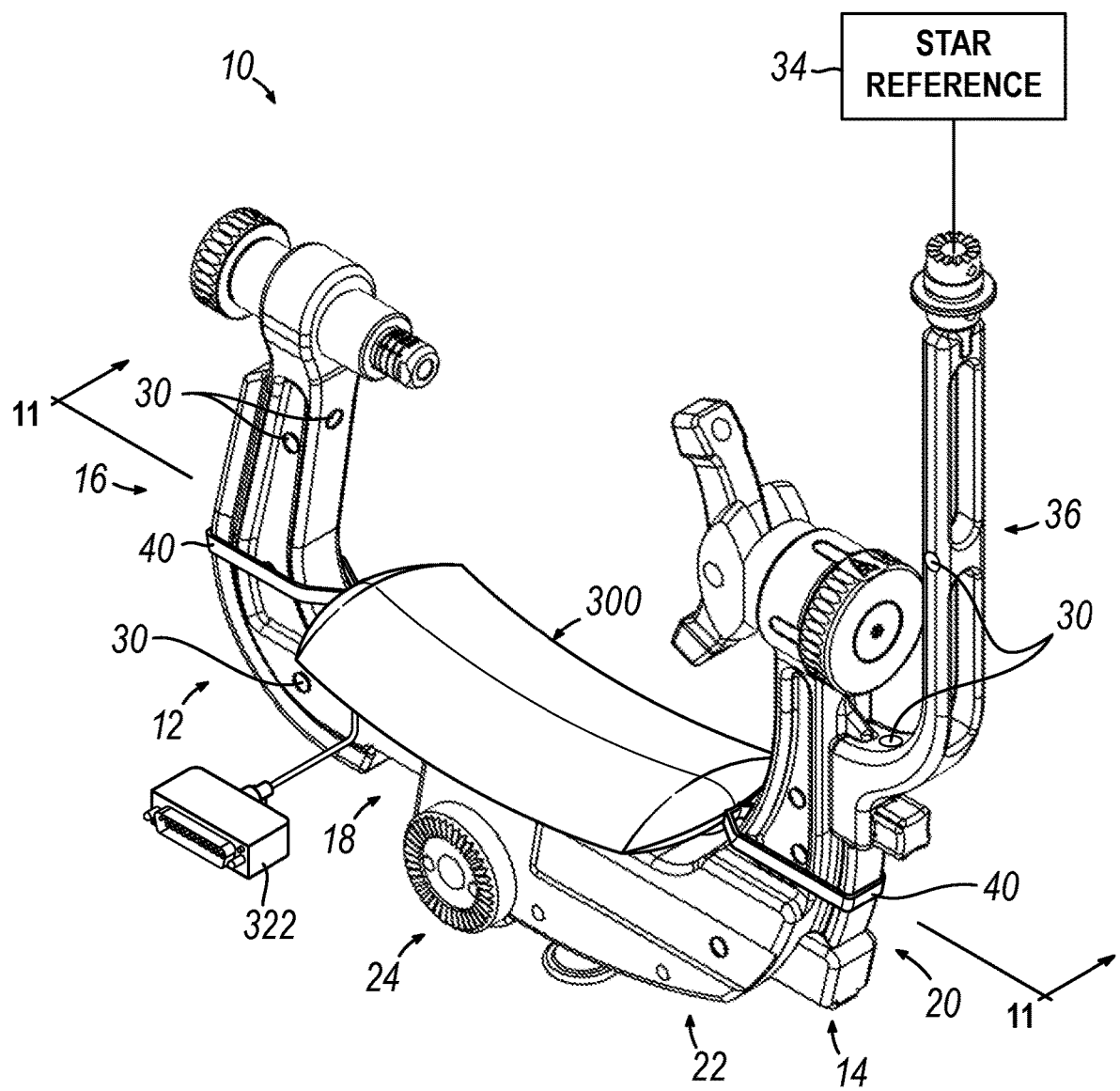
FIG. 10 depicts a front perspective view of a fourth exemplary HFD having the skull clamp of FIG. 2 with integrated MRI markers and further having a conforming bag usable with the skull clamp with an MM coil disposed within the bag.
Figure 11:
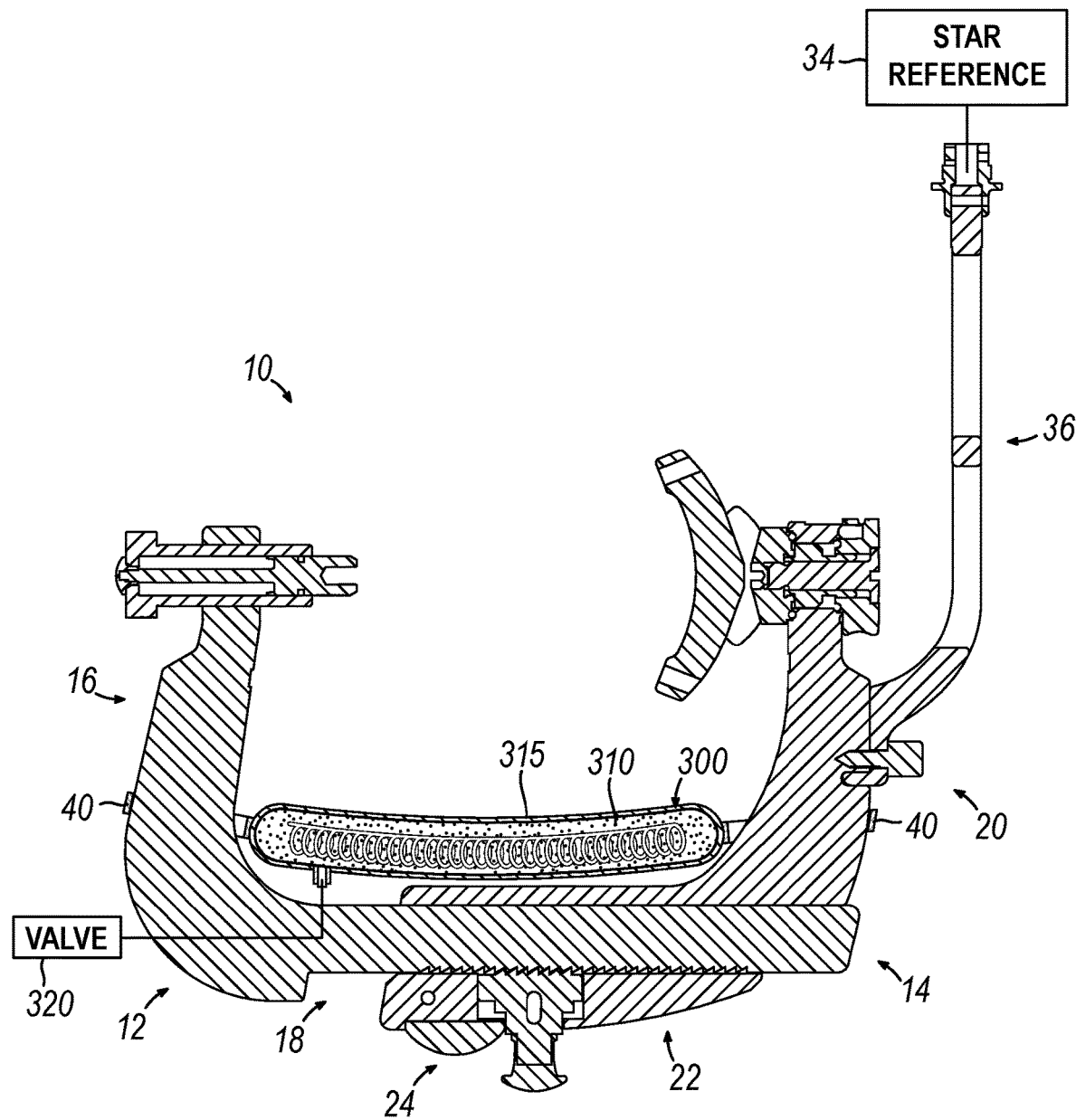
FIG. 11 depicts a cross-sectional view of the HFD of FIG. 10, taken along section line 11-11 in FIG. 10.

FIGS. 10 and 11 illustrate another exemplary configuration for an HFD, where skull clamp (10) is combined with a conforming bag (300). Conforming bag (300) may also be referred to from time to time as a granule bag or bean bag or vacuum bag. In the present example, skull clamp (10) includes Mill markers (30) as described above. Additionally, skull clamp (10) includes support arm (36) and selectively connectable primary reference (34) for use with the navigation system. As mentioned above, primary reference (34) is an active reference in some versions, and a passive reference in other versions. Bag (300) can also be used with other skull clamps or HFDs, including but not limited to skull clamps (110, 210) described above.

As shown, bag (300) is positioned within the U-shaped void or space defined by skull clamp (10). Attachment features (40) are configured for selectively connecting bag (300) with skull clamp (10). In the present example, attachment features (40) are configured so that bag (300) is positioned beneath the patient's head, it being understood that the patient may be secured with skull clamp (10) in a variety of positions depending on the procedure. Stated another way, bag (300) is positioned between the patient's head and a base of the skull clamp defined by the lateral portions described above. In some versions, bag (300) is fastened with skull clamp (10), while in other versions bag (300) is not fixed with skull clamp (10) but instead is positioned adjacent to or in contact with skull clamp (10). For instance, in versions where bag (300) is not fixed with skull clamp (10), attachment features (40) are omitted.

Bag (300) in FIG. 11 is shown in cross-section to reveal internal components. For instance, within bag (300) is granular material (315) that may take a variety of forms. Bag (300) includes a valve (320) that is configured to permit a vacuum to be applied to bag (300) such that bag (300) can adopt a rigid form once the air within bag (300) has been evacuated. In this manner, bag (300) is conformable to a patient's head supported by bag (300) such that bag may adopt more of a U-shape. Also, in the illustrated version, bag (300) includes Mill coil (310). In the present example, coil (310) is located in the same lumen, cavity, or space in which granular material (315) is located. In some other versions, bag (300) can be modified such that coil (310) is retainable in a separate lumen, cavity, or space than granular material (315). Coil (310) is configured with interface (322) as seen in FIG. 10. Interface (322) is configured to receive power form a power source such as a connection with computing device (51) that may power coil (310) by way of a battery power supply or connection to a standard electrical receptacle. Interface (322) is further configured to transmit and/or receive data, for instance by way of its connection with computing device (51) or other computing type device. In some versions, interface (322) includes serial data features for transmission of data, as well as electrical power features for receiving power to power coil (310). In other examples, data and power may be communicated independently by separate interfaces. In the present example interface (322) includes a length of cord that attaches with bag and extends within the bag to connect with coil (310) directly or indirectly through another device, such as a printed circuit board that includes connections to coil (310). Still in some other versions interface (322) is substantially flush with the bag's exterior surface. In the present example, vacuum applied to bag (300) via valve (320) can be used for patient head positioning, but such vacuum could instead or in addition be used for positioning coil (310). Where used for positioning coil (310), for example, it can be desirable to both locate coil (310) close to the operation site or area of interest on the patient and to secure coil (310) from movement or shifting to obtain acceptable imaging results and/or quality. By locating coil (310) within a bag that is conformable to the shape of the patient's head, coil (310) is positionable close to the area of interest for imaging and procedure, which positively impacts the quality of the imaging output.

FIG. 12 illustrates another exemplary conforming bag (301) that is usable with a skull clamp, such as skull clamps (10, 110, 210), to form another exemplary configuration for an HFD. For instance, bag (301) may replace bag (300) shown in FIGS. 10 and 11. Bag (301) is constructed in the same manner as bag (300), but with the addition of MRI markers (330) positioned within the bag (301). In this respect, bag (301) in FIG. 12 is shown in cross-section to reveal internal components. In the present example, markers (330) are located in the same lumen, cavity, or space in which granular material (315) is located. In some other versions, bag (301) can be modified such that markers (330) are retainable in a separate lumen, cavity, or space than granular material (315).

With the incorporation of MRI markers (330), registration and re-registration of the patient, both initially and after intra-operative scans, can be achieved in the same or similar manner as described above with respect to skull clamp (10). Having MR markers (330) in conformable bag (301) allows MR markers to be located closer to the head of the patient, which can provide more accurate registration and re-registration with the images. In addition, image quality is also positively impacted based on coil (310) being within bag (301) and positioned close to the patient's head and area of interest by conforming bag (301) to the shape of the patient's head. Because bag (301) is conformable, MR markers (330) are not fixed relative to other markers in the skull clamp or primary reference (34). However, when used in conjunction with a skull clamp having incorporated markers that remain fixed and a primary reference (34) that attaches with the skull clamp at the same location each time, the navigation system's software can determine the spatial location of MR markers (330) by calculating the change in their location from the baseline location programmed into the software for this particular HFD equipment configuration.

FIG. 13 illustrates another exemplary conforming bag (302) filled with granular material (315) that is usable with a skull clamp, such as skull clamps (10, 110, 210), to form another exemplary configuration for an HFD. For instance, bag (302) may replace bag (300) shown in FIGS. 10 and 11. Bag (302) is constructed in the same manner as bag (300), but with the addition of fiducial markers (332) positioned along an outer surface of bag (302). In this respect, bag (302) in FIG. 13 is shown with coil (310) in phantom to indicate that coil (310) is located within bag (302) while fiducial markers (332) are located on the outside surface of bag (302).

With the incorporation of fiducial markers (332), registration and re-registration of the patient, both initially and after intra-operative scans, can be achieved in the same or similar manner as described above with respect to skull clamp (110). Having fiducial markers (332) in conformable bag (302) allows fiducial markers to be located closer to the head of the patient, which can provide more accurate registration and re-registration with the images. Because bag (302) is conformable, fiducial markers (332) are not fixed relative to other markers in the skull clamp or primary reference (34). However, when used in conjunction with a skull clamp having incorporated markers that remain fixed and a primary reference (34) that attaches with the skull clamp at the same location each time, the navigation system's software can determine the spatial location of fiducial markers (332) by calculating the change in their location from the baseline location programmed into the software for this particular HFD equipment configuration. To aid in this calculation, a probe of the navigation system can be used to contact fiducial markers (332) directly or through the sterile drapes to inform the navigation system of the location of fiducial markers (332) relative to primary reference (34).

FIG. 14 illustrates another exemplary conforming bag (303) filled with granular material (315) that is usable with a skull clamp, such as skull clamps (10, 110, 210), to form another exemplary configuration for an HFD. For instance, bag (303) may replace bag (300) shown in FIGS. 10 and 11. Bag (303) is constructed in the same manner as bag (300), but with the addition of fiducial markers (332) positioned along an outer surface of bag (303), and with MRI markers (330) located within bag (303). In this respect, bag (303) in FIG. 14 is shown with coil (310) and MRI markers (330) in phantom to indicate that coil (310) and MRI markers (330) are located within bag (303) while fiducial markers (332) are located on the outside surface of bag (303). In the present example, markers (330) and coil (310) are located in the same lumen, cavity, or space in which granular material (315) is located. In some other versions, bag (303) can be modified such that markers (330) and/or coil (310) are retainable in a separate lumen, cavity, or space than granular material (315).

With the incorporation of MRI markers (330) and fiducial markers (332), registration and re-registration of the patient, both initially and after intra-operative scans, can be achieved in the same or similar manner as described above with respect to skull clamp (210). Having markers (330, 332) in conformable bag (303) allows markers to be located closer to the head of the patient, which can provide more accurate registration and re-registration with the images. Because bag (303) is conformable, markers (330, 332) are not fixed relative to other markers in the skull clamp or primary reference (34). However, when used in conjunction with a skull clamp having incorporated markers that remain fixed and a primary reference (34) that attaches with the skull clamp at the same location each time, the navigation system's software can determine the spatial location of markers (330, 332) by calculating the change in their location from the baseline location programmed into the software for this particular HFD equipment configuration. To aid in this calculation with respect to fiducial markers (332), a probe of the navigation system can be used to contact fiducial markers (332) directly or through the sterile drapes to inform the navigation system of the location of fiducial markers (332) relative to primary reference (34). This would not be needed for MR markers (330) as they would be apparent in the output of the MRI scan that is provided to the navigation system.

Figure 15:
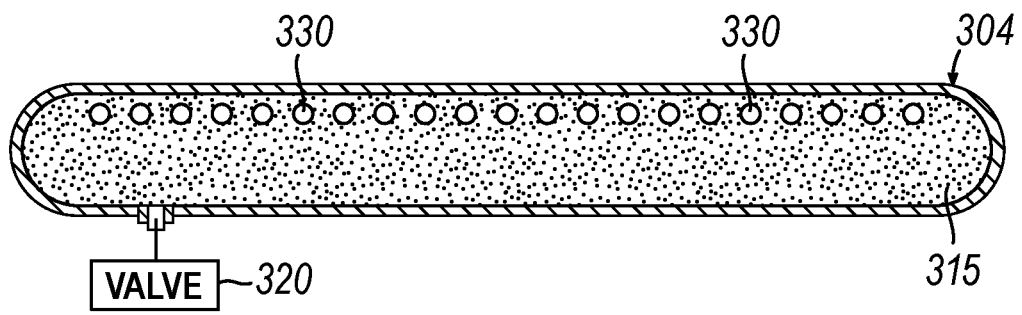
FIG. 15 depicts a cross-sectional view of another exemplary conforming bag for use with the skull clamp of FIG. 10, showing MRI markers disposed within the bag.

FIG. 15 illustrates another exemplary conforming bag (304) filled with granular material (315) that is usable with a skull clamp, such as skull clamps (10, 110, 210), to form another exemplary configuration for an HFD. For instance, bag (304) may replace bag (300) shown in FIGS. 10 and 11. Bag (304) is constructed in the same manner as bag (300), but without coil (310) within bag (304) and with the addition of MRI markers (330) positioned within the bag (304). In this respect, bag (304) in FIG. 15 is shown in cross-section to reveal internal components. In the present example, markers (330) are located in the same lumen, cavity, or space in which granular material (315) is located. In some other versions, bag (304) can be modified such that markers (330) are retainable in a separate lumen, cavity, or space than granular material (315). When imaging using bag (304), an MRI coil is provided separately as part of the imaging equipment.

With the incorporation of MM markers (330), registration and re-registration of the patient, both initially and after intra-operative scans, can be achieved in the same or similar manner as described above with respect to skull clamp (10). Having MR markers (330) in conformable bag (304) allows MR markers to be located closer to the head of the patient, which can provide more accurate registration and re-registration with the images. Because bag (304) is conformable, MR markers (330) are not fixed relative to other markers in the skull clamp or primary reference (34). However, when used in conjunction with a skull clamp having incorporated markers that remain fixed and a primary reference (34) that attaches with the skull clamp at the same location each time, the navigation system's software can determine the spatial location of MR markers (330) by calculating the change in their location from the baseline location programmed into the software for this particular HFD equipment configuration.

Figure 16:
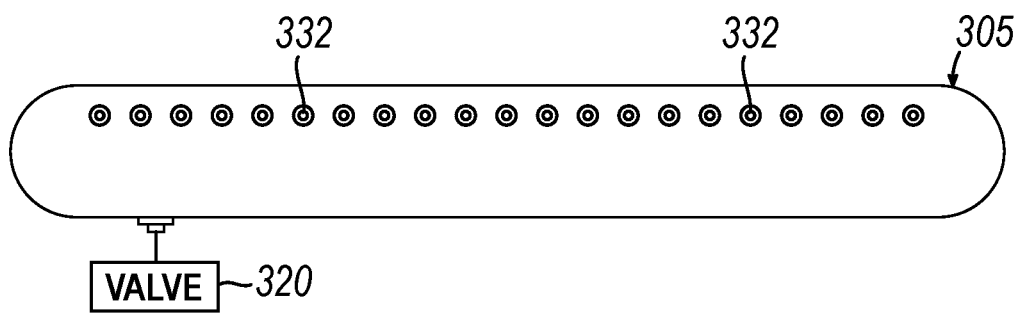
FIG. 16 depicts a side view of another exemplary conforming bag for use with the skull clamp of FIG. 10, showing fiducial markers located on the outside surface of the bag.

FIG. 16 illustrates another exemplary conforming bag (305) filled with granular material (315) that is usable with a skull clamp, such as skull clamps (10, 110, 210), to form another exemplary configuration for an HFD. For instance, bag (305) may replace bag (300) shown in FIGS. 10 and 11. Bag (305) is constructed in the same manner as bag (300), but without coil (310) and with the addition of fiducial markers (332) positioned along an outer surface of bag (305). When imaging using bag (305), an Mill coil is provided separately as part of the imaging equipment.

With the incorporation of fiducial markers (332), registration and re-registration of the patient, both initially and after intra-operative scans, can be achieved in the same or similar manner as described above with respect to skull clamp (110). Having fiducial markers (332) in conformable bag (305) allows fiducial markers to be located closer to the head of the patient, which can provide more accurate registration and re-registration with the images. Because bag (305) is conformable, fiducial markers (332) are not fixed relative to other markers in the skull clamp or primary reference (34). However, when used in conjunction with a skull clamp having incorporated markers that remain fixed and a primary reference (34) that attaches with the skull clamp at the same location each time, the navigation system's software can determine the spatial location of fiducial markers (332) by calculating the change in their location from the baseline location programmed into the software for this particular HFD equipment configuration. To aid in this calculation, a probe of the navigation system can be used to contact fiducial markers (332) directly or through the sterile drapes to inform the navigation system of the location of fiducial markers (332) relative to primary reference (34).

Figure 17:
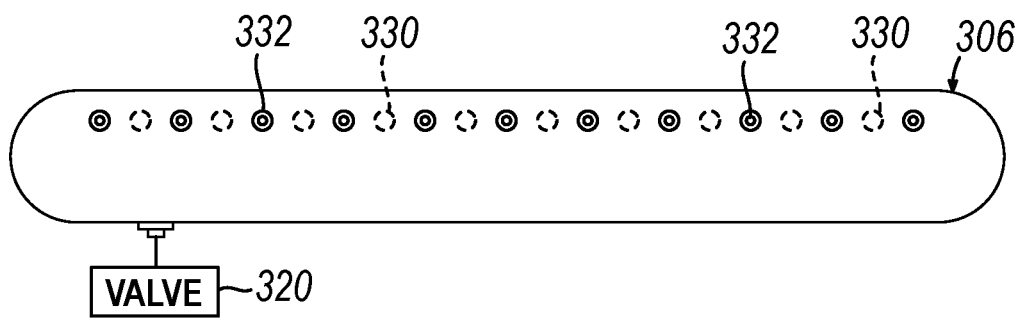
FIG. 17 depicts a side view of another exemplary conforming bag for use with the skull clamp of FIG. 10, showing MM markers disposed within the bag and fiducial markers located on the outside surface of the bag.
Figure 22:
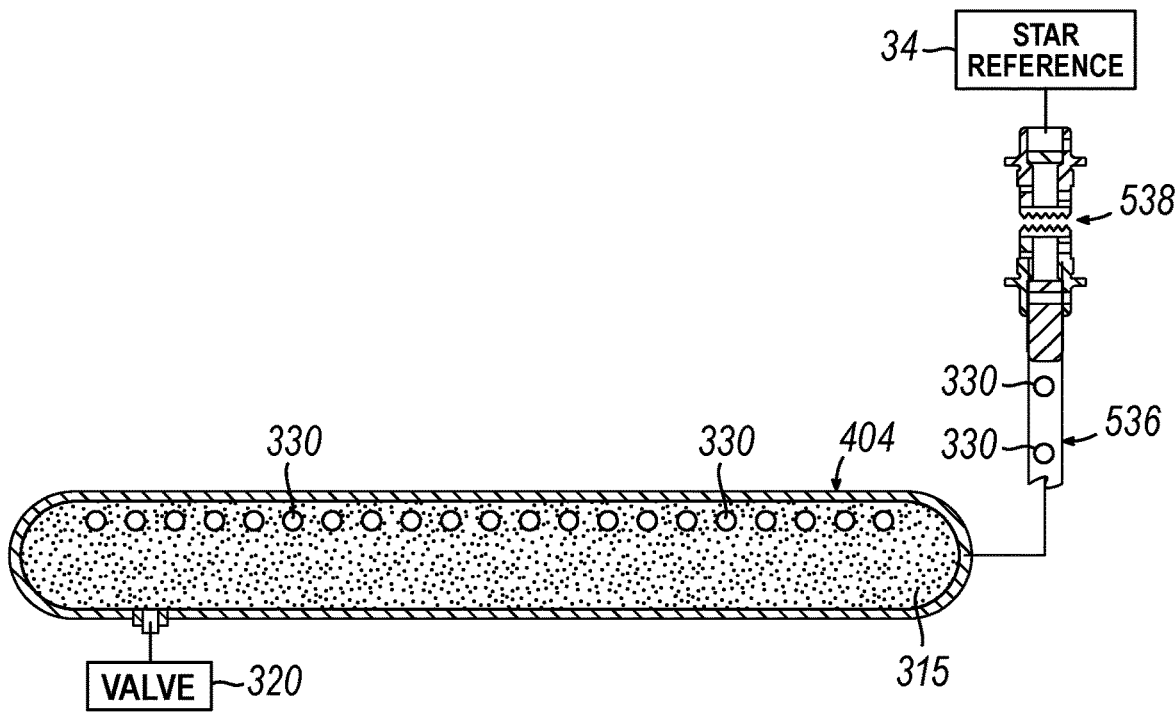
FIG. 22 depicts a cross-sectional view of a ninth exemplary HFD in the form of a conforming bag, showing MM markers disposed within the bag.

FIG. 17 illustrates another exemplary conforming bag (306) filled with granular material (315) that is usable with a skull clamp, such as skull clamps (10, 110, 210), to form another exemplary configuration for an HFD. For instance, bag (306) may replace bag (300) shown in FIGS. 10 and 11. Bag (306) is constructed in the same manner as bag (300), but without coil (310) and with the addition of fiducial markers (332) positioned along an outer surface of bag (306), and with Mill markers (330) located within bag (306). In this respect, bag (306) in FIG. 22 is shown with MRI markers (330) in phantom to indicate that MRI markers (330) are located within bag (306) while fiducial markers (332) are located on the outside surface of bag (306). In the present example, markers (330) are located in the same lumen, cavity, or space in which granular material (315) is located. In some other versions, bag (306) can be modified such that markers (330) are retainable in a separate lumen, cavity, or space than granular material (315). When imaging using bag (306), an MRI coil is provided separately as part of the imaging equipment.

With the incorporation of MRI markers (330) and fiducial markers (332), registration and re-registration of the patient, both initially and after intra-operative scans, can be achieved in the same or similar manner as described above with respect to skull clamp (210). Having markers (330, 332) in conformable bag (306) allows markers to be located closer to the head of the patient, which can provide more accurate registration and re-registration with the images. Because bag (306) is conformable, markers (330, 332) are not fixed relative to other markers in the skull clamp or primary reference (34). However, when used in conjunction with a skull clamp having incorporated markers that remain fixed and a primary reference (34) that attaches with the skull clamp at the same location each time, the navigation system's software can determine the spatial location of markers (330, 332) by calculating the change in their location from the baseline location programmed into the software for this particular HFD equipment configuration. To aid in this calculation with respect to fiducial markers (332), a probe of the navigation system can be used to contact fiducial markers (332) directly or through the sterile drapes to inform the navigation system of the location of fiducial markers (332) relative to primary reference (34). This would not be needed for MR markers (330) as they would be apparent in the output of the MRI scan that is provided to the navigation system.

IV. Exemplary Conforming Bag HFDs with Integrated Features

Figure 18:
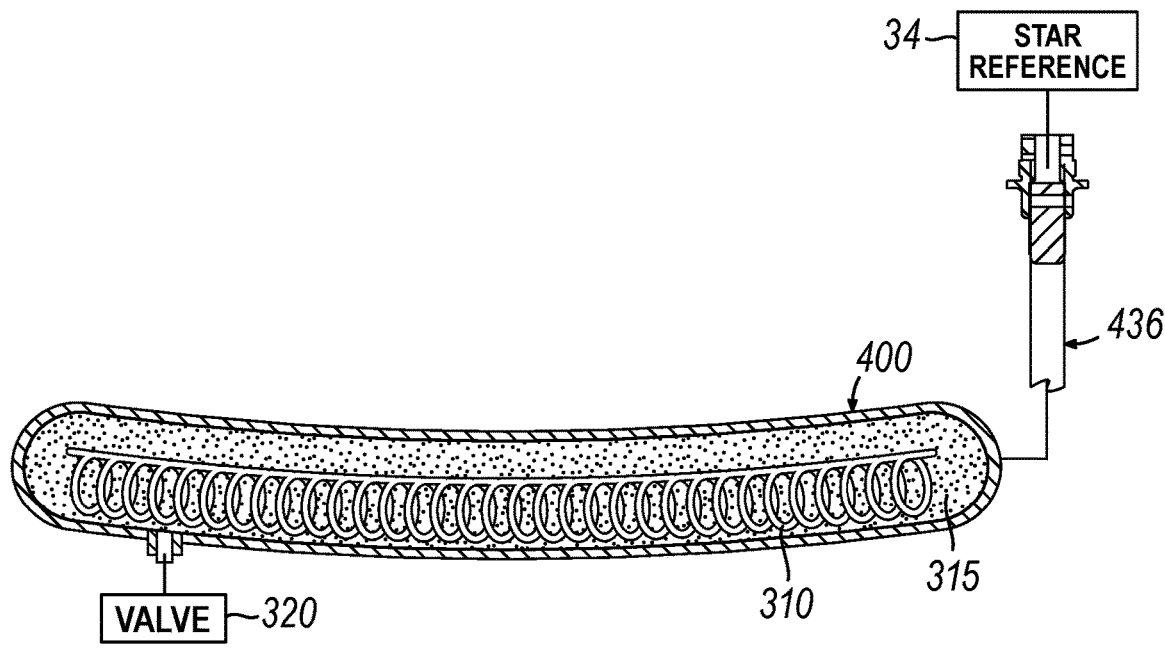
FIG. 18 depicts a cross-sectional view of a fifth exemplary HFD in the form of a conforming bag, showing an Mill coil disposed within the bag.

FIG. 18 illustrates another exemplary configuration for an HFD, where the HFD is defined by a conforming bag (400). Conforming bag (400) may also be referred to from time to time as a granule bag or bean bag. In the present example, a support arm or holder (436) is selectively connectable with the bag (400). For example, bag (400) can be equipped with an interface on its outer surface for connecting with a corresponding interface incorporated with support arm (436). In another example, support arm (436) can be equipped with a clamping feature on the end opposite to the primary reference (34). This clamping feature can be configured to securely connect with a portion of bag (400) when bag (400) has been subjected to vacuum and adopted its rigid state. Still in other versions, arm (436) can be permanently attached with bag (400). In view of the teachings herein, other ways to selectively couple or connect support arm (436) with bag (400) will be apparent to those of ordinary skill in the art.

Primary reference (34) for use with the navigation system is selectively connectable with support arm (436). As mentioned above, primary reference (34) is an active reference in some versions, and a passive reference in other versions. In the present example, bag (400) is usable for patient support and/or stabilization without the use of a skull clamp or other clamping or pinning device. In this manner bag (400) can be suited for very young patients from birth to about 6 months. Of course, bag (400) can be used with other patient populations as well. In the present example, bag (400) is configured so that bag (400) is positioned beneath the patient's head, it being understood that the patient may be in a variety of positions depending on the procedure. Stated another way, bag (400) is positioned subjacent to the patient's head.

Bag (400) in FIG. 18 is shown in cross-section to reveal internal components. For instance, within bag (400) is granular material (315) that may take a variety of forms. Bag (400) includes a valve (320) that is configured to permit a vacuum to be applied to bag (400) such that bag (400) can adopt a rigid form once the air within bag (400) has been evacuated. In this manner, bag (400) is conformable to a patient's head supported by bag (400). Also, in the illustrated version, bag (400) includes MRI coil (310). In the present example, coil (310) is located in the same lumen, cavity, or space in which granular material (315) is located. In some other versions, bag (400) can be modified such that coil (310) is retainable in a separate lumen, cavity, or space than granular material (315). In the present example, vacuum applied to bag (400) via valve (320) can be used for patient head positioning, but such vacuum could instead or in addition be used for positioning coil (310). Where used for positioning coil (310), for example, it can be desirable to both locate coil (310) close to the operation site or area of interest on the patient, and to secure coil (310) from movement or shifting to obtain acceptable imaging results and/or quality. By locating coil (310) within a bag that is conformable to the shape of the patient's head, coil (310) is positionable close to the area of interest for imaging and procedure, which positively impacts the quality of the imaging output.

Figure 19:
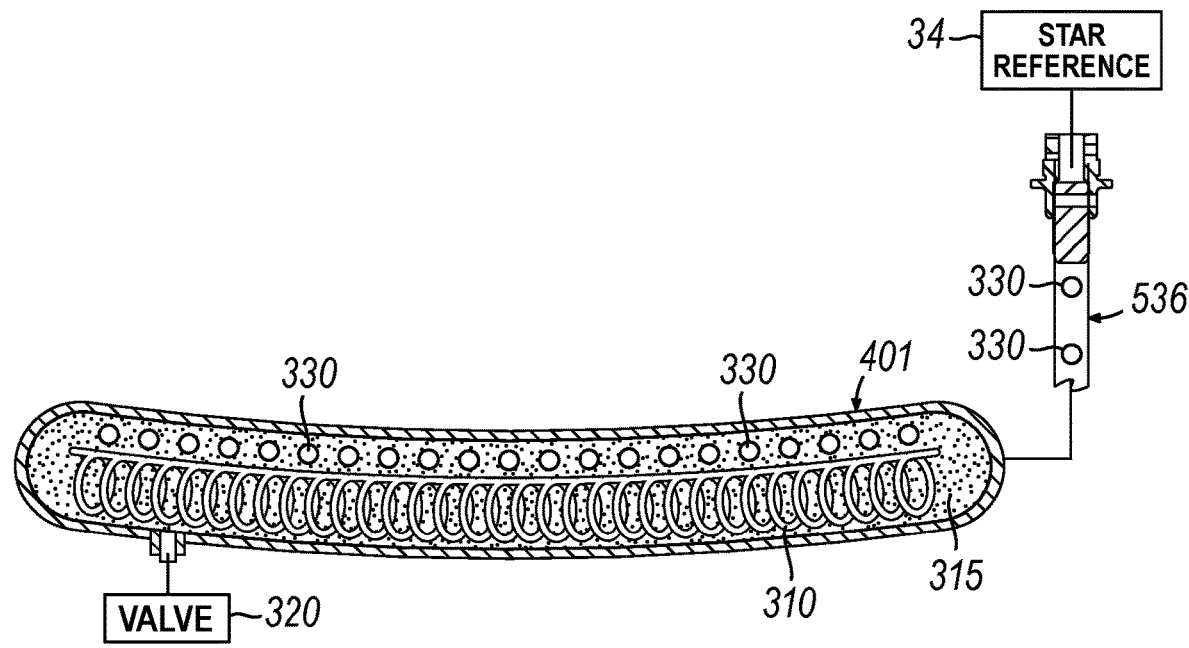
FIG. 19 depicts a cross-sectional view of a sixth exemplary HFD in the form of a conforming bag, showing both an MM coil and MM markers disposed within the bag.

FIG. 19 illustrates another exemplary conforming bag (401) defining an HFD. Bag (401) is constructed in the same manner as bag (400), but with the addition of MRI markers (330) positioned within the bag (401). In this respect, bag (401) in FIG. 19 is shown in cross-section to reveal internal components. In the present example, markers (330) are located in the same lumen, cavity, or space in which granular material (315) is located. In some other versions, bag (401) can be modified such that markers (330) are retainable in a separate lumen, cavity, or space than granular material (315).

With the incorporation of MRI markers (330), registration and re-registration of the patient, both initially and after intra-operative scans, can be achieved in the same or similar manner as described above with respect to skull clamp (10). Additional to MRI markers (330) within bag (401), bag (401) includes support arm (536) that also includes MRI markers (330). Having MR markers (330) in conformable bag (401) allows MR markers to be located closer to the head of the patient, which can provide more accurate registration and re-registration with the images. Because bag (401) is conformable, MR markers (330) are not fixed relative to other markers in the HFD or primary reference (34). However, support arm (536) includes markers (330) that remain fixed relative to primary reference (34). Therefore, the navigation system's software can determine the spatial location of MR markers (330) within bag (401). For instance, MR markers (330) will appear in the MRI output provided to the navigation system. With primary reference (34) attached with bag (401), the optical camera of the navigation system locates primary reference (34). Because certain MR markers (330) are located on support arm (536) and fixed relative to primary reference (34), the navigation system's software calculates the change in the location of MR markers (330) within bag (401) based on the change relative to MR markers (330) on support arm (536). This information is then used for patient registration.

Figure 20:
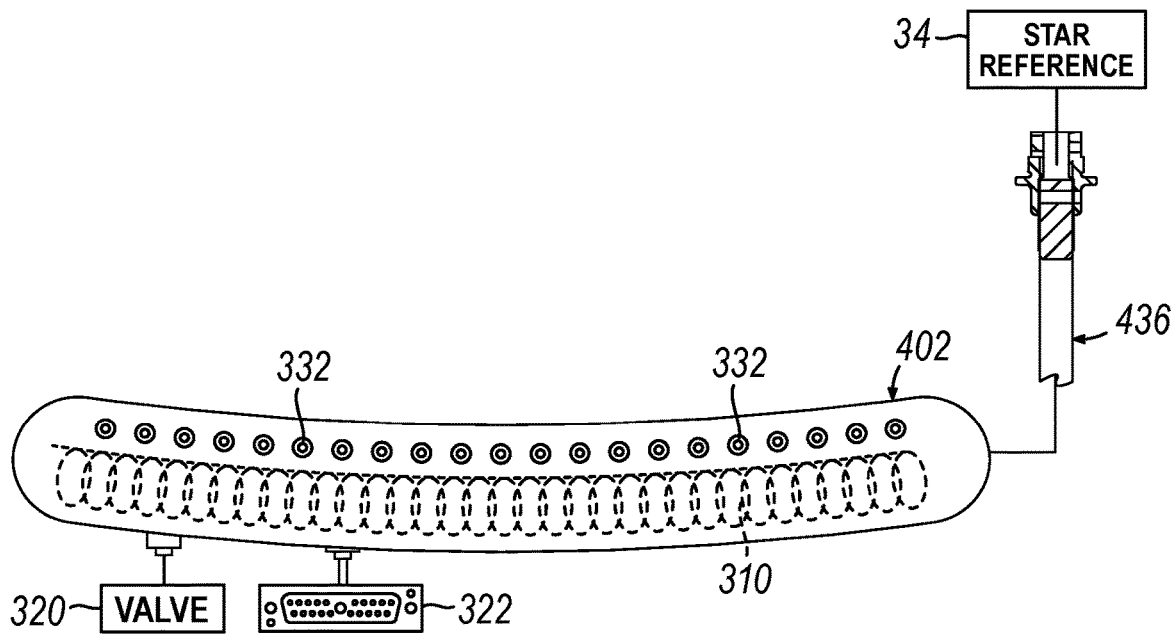
FIG. 20 depicts a side view of a seventh exemplary HFD in the form of a conforming bag, showing both an Mill coil disposed within the bag and fiducial markers located on the outside surface of the bag.

FIG. 20 illustrates another exemplary conforming bag (402) filled with granular material (315) defining an HFD. Bag (402) is constructed in the same manner as bag (400), but with the addition of fiducial markers (332) positioned along an outer surface of bag (402). In this respect, bag (402) in FIG. 20 is shown with coil (310) in phantom to indicate that coil (310) is located within bag (402) while fiducial markers (332) are located on the outside surface of bag (402).

With the incorporation of fiducial markers (332), registration and re-registration of the patient, both initially and after intra-operative scans, can be achieved in the same or similar manner as described above with respect to skull clamp (110). Having fiducial markers (332) in conformable bag (402) allows fiducial markers to be located closer to the head of the patient, which can provide more accurate registration and re-registration with the images. Because bag (402) is conformable, fiducial markers (332) are not fixed relative to other markers in the HFD or primary reference (34). However, the navigation system's software can determine the spatial location of fiducial markers (332) of bag (402). To aid in this calculation with respect to fiducial markers (332), a probe of the navigation system can be used to contact fiducial markers (332) directly or through the sterile drapes to inform the navigation system of the location of fiducial markers (332) relative to primary reference (34). This information is then used for patient registration.

Figure 21:
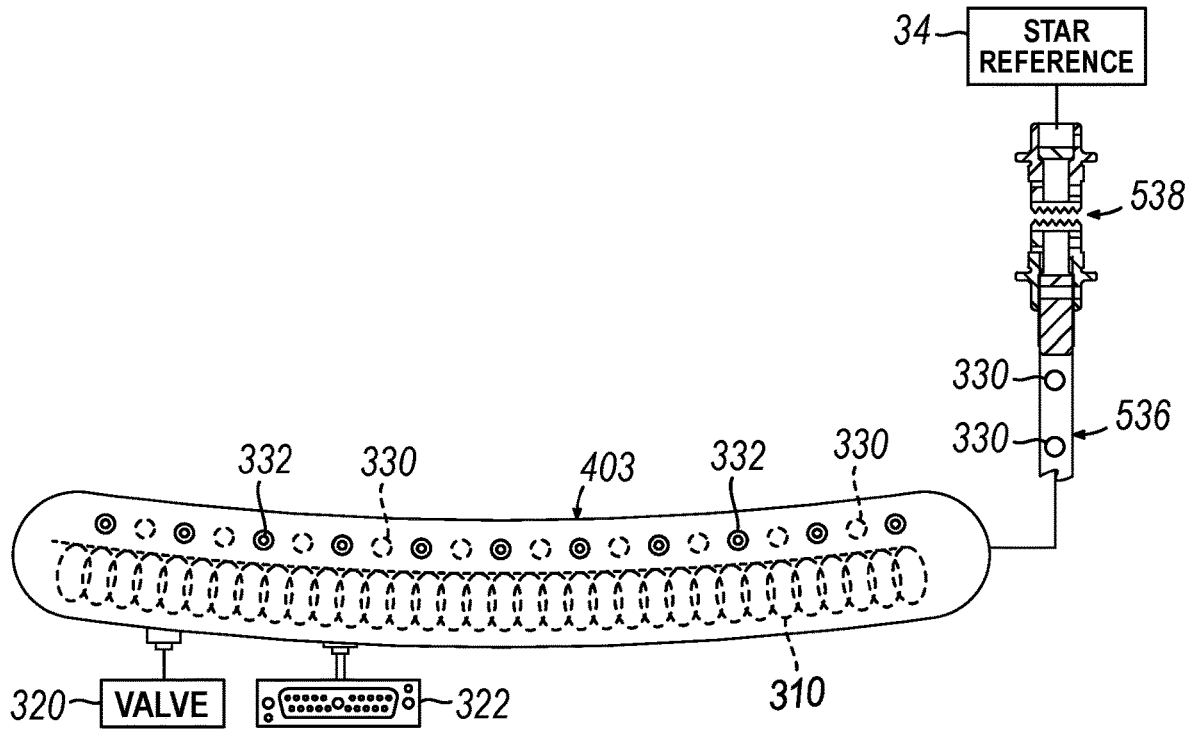
FIG. 21 depicts a side view of an eighth exemplary HFD in the form of a conforming bag, showing both an MRI coil and MRI markers disposed within the bag and fiducial markers located on the outside surface of the bag.

FIG. 21 illustrates another exemplary conforming bag (403) filled with granular material (315) defining an HFD. Bag (403) is constructed in the same manner as bag (400), but with the addition of fiducial markers (332) positioned along an outer surface of bag (403), and with MRI markers (330) located within bag (403). In this respect, bag (403) in FIG. 26 is shown with coil (310) and MRI markers (330) in phantom to indicate that coil (310) and MRI markers (330) are located within bag (403) while fiducial markers (332) are located on the outside surface of bag (403). In the present example, markers (330) and coil (310) are located in the same lumen, cavity, or space in which granular material (315) is located. In some other versions, bag (403) can be modified such that markers (330) and/or coil (310) are retainable in a separate lumen, cavity, or space than granular material (315).

With the incorporation of MRI markers (330) and fiducial markers (332), registration and re-registration of the patient, both initially and after intra-operative scans, can be achieved in the same or similar manner as described above with respect to bags (401, 402). Additional to MRI markers (330) within bag (403), bag (403) includes support arm (536) that also includes MRI markers (330). In the present example, support arm (536) is shown with an interface (538) that is configured to connect with primary reference (34). In this way primary reference (34) can be removed and reinstalled in a repeatable fashion onto interface (538).

FIG. 22 illustrates another exemplary conforming bag (404) that defines an HFD. Bag (404) is constructed in the same manner as bag (400), but without coil (310) within bag (404) and with the addition of MRI markers (330) positioned within the bag (304). In this respect, bag (404) in FIG. 22 is shown in cross-section to reveal internal components. In the present example, markers (330) are located in the same lumen, cavity, or space in which granular material (315) is located. In some other versions, bag (404) can be modified such that markers (330) are retainable in a separate lumen, cavity, or space than granular material (315). When imaging using bag (404), an MRI coil is provided separately as part of the imaging equipment.

With the incorporation of MRI markers (330), registration and re-registration of the patient, both initially and after intra-operative scans, can be achieved in the same or similar manner as described above with respect to bag (401). Additional to MRI markers (330) within bag (404), bag (404) includes support arm (536) that also includes MRI markers (330). In the present example, support arm (536) is shown with an interface (538) that is configured to connect with primary reference (34). In this way primary reference (34) can be removed and reinstalled in a repeatable fashion onto interface (538).

Figure 23:
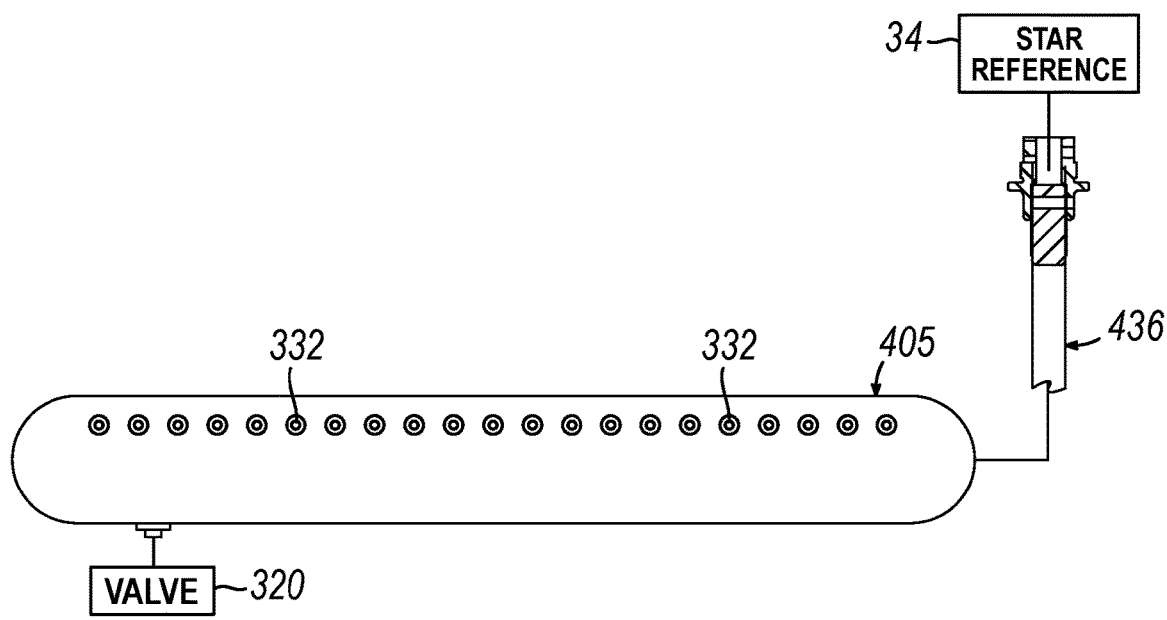
FIG. 23 depicts a side view of a tenth exemplary HFD in the form of a conforming bag, showing fiducial markers located on the outside surface of the bag.

FIG. 23 illustrates another exemplary conforming bag (405) filled with granular material (315) that defines an HFD. Bag (405) is constructed in the same manner as bag (400), but without coil (310) and with the addition of fiducial markers (332) positioned along an outer surface of bag (405). When imaging using bag (405), an MRI coil is provided separately as part of the imaging equipment. Additional to fiducial markers (332) along the outer surface of bag (405), bag (405) is connectable with support arm (436) connectable with primary reference (34). With the incorporation of fiducial markers (332), registration and re-registration of the patient, both initially and after intra-operative scans, can be achieved in the same or similar manner as described above with respect to bag (402).

Figure 24:
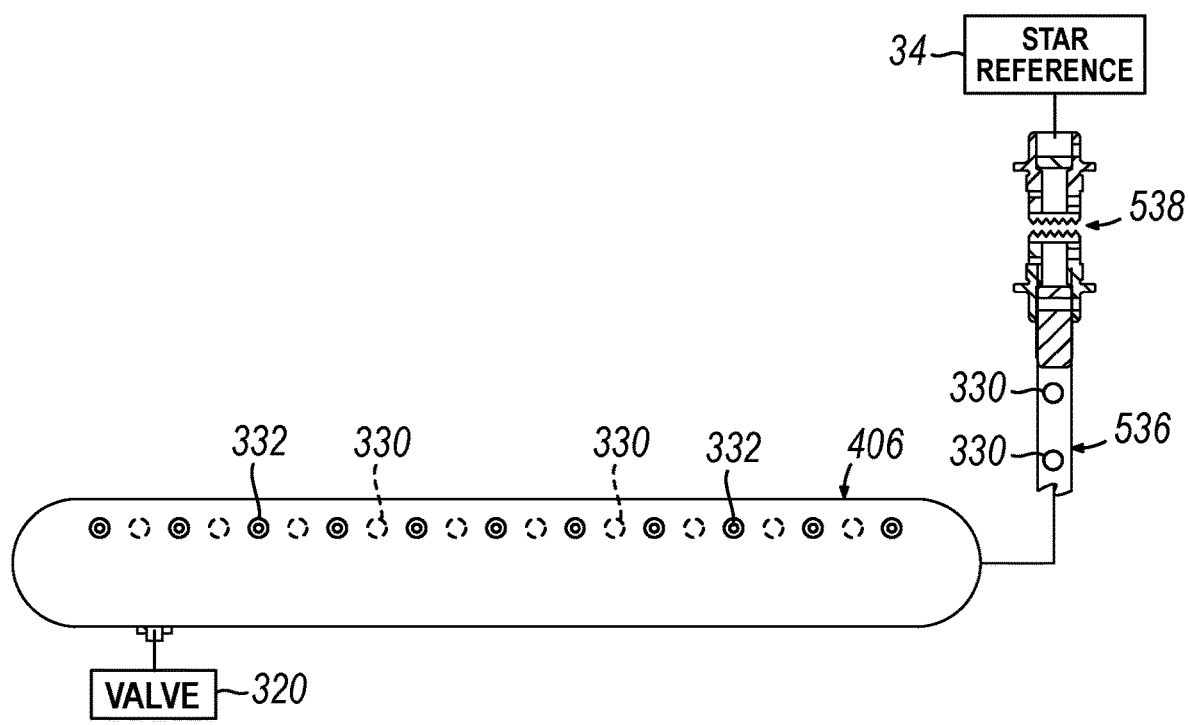
FIG. 24 depicts a side view of an eleventh exemplary HFD in the form of a conforming bag, showing MRI markers disposed within the bag and fiducial markers located on the outside surface of the bag.

FIG. 24 illustrates another exemplary conforming bag (406) filled with granular material (315) that defines an HFD. Bag (406) is constructed in the same manner as bag (400), but without coil (310) and with the addition of fiducial markers (332) positioned along an outer surface of bag (406), and with MRI markers (330) located within bag (406). In this respect, bag (406) in FIG. 24 is shown with MRI markers (330) in phantom to indicate that MRI markers (330) are located within bag (406) while fiducial markers (332) are located on the outside surface of bag (406). In the present example, markers (330) are located in the same lumen, cavity, or space in which granular material (315) is located. In some other versions, bag (406) can be modified such that markers (330) are retainable in a separate lumen, cavity, or space than granular material (315). When imaging using bag (406), an MRI coil is provided separately as part of the imaging equipment.

With the incorporation of MRI markers (330) and fiducial markers (332), registration and re-registration of the patient, both initially and after intra-operative scans, can be achieved in the same or similar manner as described above with respect to bags (404, 405). Additional to MRI markers (330)

within bag (406), bag (406) includes support arm (536) that also includes MRI markers (330). In the present example, support arm (536) is shown with an interface (538) that is configured to connect with primary reference (34). In this way primary reference (34) can be removed and reinstalled in a repeatable fashion onto interface (538).

The above examples have shown and described configurations for navigation guided procedures where either or both MRI markers and fiducial markers are used where these markers are formed as part of, attached to, or otherwise incorporated with or into an HFD that may be in the form of a skull clamp, conformable bag, or other configuration. In some instances, such an HFD can be configured with one or more markers where these markers serve both as MM markers and fiducial markers. For instance, any of the markers illustrated could be modified such that the markers are both MRI detectable and able to serve as fiducial markers.

In addition, for those exemplary conformable bag HFDs that incorporate a MRI coil, such as coil (310), vacuum applied to the bag via valve (320) can be used for patient head positioning, but such vacuum could instead or in addition be used for positioning coil (310). Where used for positioning coil (310), for example, it can be desirable to both locate coil (310) close to the operation site or area of interest on the patient, and to secure coil (310) from movement or shifting to obtain acceptable imaging results and/or quality. By locating coil (310) within a bag that is conformable to the shape of the patient's head, coil (310) is positionable close to the area of interest for imaging and procedure, which positively impacts the quality of the imaging output.

For those exemplary conformable bag HFD that incorporate a support arm, such as support arm (436, 536), the support arm can be constructed as part of the bag in some versions such that the support arm is not removable from the bag. In other versions, the support arm is selectively connectable or attachable with the bag. In these versions, the support arm may include a clamping feature at its end that connects with the bag, or the bag may be constructed with an interface that engages a complementary interface of the support arm. In view of the teachings herein, other ways to attach a support arm, either permanently or removably, will be apparent to those of ordinary skill in the art.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. The following examples are being provided for nothing more than merely illustrative purposes. It is contemplated that the various teachings herein may be arranged and applied in numerous other ways. It is also contemplated that some variations may omit certain features referred to in the below examples.

Example 1

A device for stabilizing a head of a patient during a medical procedure comprises (a) a skull clamp having at least one first integrated marker positioned on the device. The at least one first integrated marker is detectable by an MRI scanner. The at least one first integrated marker provides at least one first reference point relative to an operation site in one or more images for use in a navigation guided procedure. The device further comprises (b) a primary reference marker detectable by a navigation system, wherein the primary reference marker is selectively connectable with the skull clamp in a single orientation fixed relative to the skull clamp and the at least one first integrated marker, and wherein the primary reference marker is configured to provide a reference origin for defining a position of the at least one first reference point relative to the operation site Example 2

The device Example 1 further comprising at least one second integrated marker positioned on the device. The at least one second integrated marker includes a fiducial marker that is detectable by a registration tool of the navigation system. The at least one second integrated marker provides at least one second reference point relative to the operation site in the one or more images for use in the navigation guided procedure.

Example 3

The device of Example 2, wherein the at least one first integrated marker and the at least one second integrated marker are integrally formed together as a single marker that is both detectable by an MRI scanner and detectable by the registration tool of the navigation system.

Example 4

The device of any one or more of Example 1 through Example 3, further comprising a support arm configured to receive the primary reference marker.

Example 5

The device of any one or more of Example 1 through Example 3, wherein the support arm comprises an MR marker.

Example 6

The device of any one or more of Example 1 through Example 3, wherein the device comprises a conformable bag configured to adopt a rigid configuration when subjected to vacuum.

Example 7

The device of Example 6, wherein the conformable bag comprises an MRI coil located within the conformable bag.

Example 8

The device of any one or more of Example 6 through Example 7, wherein the conformable bag comprises one or more MR markers located within the conformable bag.

Example 9

The device of any one or more of Example 6 through Example 8, wherein the conformable bag comprises one or more fiducial markers located on an exterior surface of the conformable bag.

Example 10

A patient head support for use during a medical procedure with a patient comprises: (a) a bag having an interior, wherein the bag is configured to receive a head of the patient and to conform to the head of the patient; (b) a conformable material disposed within the interior of the bag; and (c) a select one or more of (i) an MRI coil coupled to the bag and (ii) at least one marker configured for registering the patient with an image of the patient usable in a navigation system.

Example 11

The patient head support of Example 10, comprising the MM coil, wherein the MRI coil is located within the bag, wherein the patient head support is configured to position the MRI coil relative to a position of a head of the patient for use in an MRI scan.

Example 12

The patient head support of any one or more of Example 10 through Example 11, comprising the at least one marker, wherein the at least one marker includes one or more MRI markers positioned within the bag.

Example 13

The patient head support of any one or more of Example 10 through Example 12, comprising the at least one marker, wherein the at least one marker further includes one or more fiducial markers positioned on an outer surface of the bag.

Example 14

The patient head support of any one or more of Example 10 through Example 13, further comprising a primary reference marker of a navigation system, wherein the primary reference marker is selectively connectable with the bag.

Example 15

The patient head support of any one or more of Example 10 through Example 14, further comprising a support arm having an interface configured to selectively receive and retain the primary reference marker of the navigation system, wherein the support arm is couplable with the bag, and wherein the support arm comprises one or more MR markers.

Example 16

The patient head support of any one or more of Example 10 through Example 15, further comprising a skull clamp, wherein the bag is positionable within a U-shaped opening of the skull clamp.

VI. Miscellaneous

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A device for stabilizing a head of a patient during a medical procedure, wherein the device comprises:
   (a) a skull clamp having a pair of arms, each with an upright portion, a lateral portion, and an end that is configured to receive a stabilization assembly, wherein the lateral portions are translatable relative to one another to adjust a spacing of the respective upright portions to adjust a width of the skull clamp, the skull clamp further comprising at least one first integrated marker positioned along the upright portion and/or the lateral portion of a select one or more of the arms of the pair of arms, wherein the at least one first integrated marker is detectable by an MRI scanner, wherein the at least one first integrated marker is configured to provide at least one first reference point relative to an operation site in one or more images for use in a navigation guided procedure; and
   (b) a primary reference marker detectable by a navigation system, wherein the primary reference marker is selectively connectable with the skull clamp in a single orientation fixed relative to the skull clamp and the at least one first integrated marker, and wherein the primary reference marker is configured to provide a reference origin for defining a position of the at least one first reference point relative to the operation site.

2. The device of claim 1 further comprising at least one second integrated marker positioned on the device, wherein the at least one second integrated marker includes a fiducial marker that is configured to be detectable by a registration tool of the navigation system, wherein the at least one second integrated marker is configured to provide at least one second reference point relative to the operation site in the one or more images for use in the navigation guided procedure.

3. The device of claim 2, wherein the at least one first integrated marker and the at least one second integrated marker are integrally formed together as a single marker that is both detectable by an MRI scanner and detectable by the registration tool of the navigation system.

4. The device of claim 1 further comprising a support arm configured to receive the primary reference marker.

5. The device of claim 4, wherein the support arm comprises an MR marker.

6. A device for stabilizing a head of a patient during a medical procedure, wherein the device comprises:
   (a) a skull clamp having at least one first integrated marker positioned on the device, wherein the at least one first integrated marker is detectable by an MRI scanner, wherein the at least one first integrated marker is configured to provide at least one first reference point relative to an operation site in one or more images for use in a navigation guided procedure;
   (b) a primary reference marker detectable by a navigation system, wherein the primary reference marker is selectively connectable with the skull clamp in a single orientation fixed relative to the skull clamp and the at least one first integrated marker, and wherein the primary reference marker is configured to provide a reference origin for defining a position of the at least one first reference point relative to the operation site; and (c) at least one second integrated marker positioned on the device, wherein the at least one second integrated marker includes a fiducial marker that is configured to be detectable by a registration tool of the navigation system, wherein the at least one second integrated marker is configured to provide at least one second reference point relative to the operation site in the one or more images for use in the navigation guided procedure, wherein the at least one first integrated marker and the at least one second integrated marker are integrally formed together as a single marker that is both detectable by an MRI scanner and detectable by the registration tool of the navigation system.

* * * * *